(12) United States Patent
Tak et al.

(10) Patent No.: US 10,639,067 B2
(45) Date of Patent: May 5, 2020

(54) GUIDING TROCAR AND SYSTEM FOR CONNECTING TO A GUIDING TROCAR

(71) Applicant: Mofixx B.V., Enschede (NL)

(72) Inventors: Maurice Petrus Wilhelmus Tak, Enschede (NL); Jasper Boter, Enschede (NL); Hendricus Johannes Vertegaal, Enschede (NL); Marianne Gratia Meijerink-van Tilburg, Enschede (NL); Maarten Wobbe van der Werf, Enschede (NL); Joris Emanuel Nicolaas Jaspers, Bodegraven (NL); Jesse Mattan Bosma, Utrecht (NL)

(73) Assignee: Mofixx B.V., Enschede (NL)

( * ) Notice: Subject to any disclaimer, the term of this patent is extended or adjusted under 35 U.S.C. 154(b) by 148 days.

(21) Appl. No.: 15/555,906

(22) PCT Filed: Mar. 14, 2016

(86) PCT No.: PCT/NL2016/050180
§ 371 (c)(1),
(2) Date: Sep. 5, 2017

(87) PCT Pub. No.: WO2016/144180
PCT Pub. Date: Sep. 15, 2016

(65) Prior Publication Data
US 2018/0049768 A1 Feb. 22, 2018

(30) Foreign Application Priority Data
Mar. 12, 2015 (NL) .................................... 2014448

(51) Int. Cl.
*A61B 17/34* (2006.01)
*A61B 90/57* (2016.01)
(Continued)

(52) U.S. Cl.
CPC .......... *A61B 17/3415* (2013.01); *A61B 17/34* (2013.01); *A61B 90/57* (2016.02);
(Continued)

(58) Field of Classification Search
CPC . A61B 17/34; A61B 17/3415; A61B 17/3468; A61B 2017/347; A61B 17/3403;
(Continued)

(56) References Cited

U.S. PATENT DOCUMENTS

| | | | |
|---|---|---|---|
| 7,695,480 B2 * | 4/2010 | Solar | A61B 90/11 606/130 |
| 2012/0296281 A1 * | 11/2012 | Jaspers | A61B 17/3421 604/164.04 |

FOREIGN PATENT DOCUMENTS

| | | |
|---|---|---|
| DE | 19625729 A1 | 1/1998 |
| EP | 2143392 A2 | 1/2010 |
| WO | WO2011043644 A1 | 4/2011 |

* cited by examiner

*Primary Examiner* — Melanie R Tyson
(74) *Attorney, Agent, or Firm* — Bret E. Field; Bozicevic, Field & Francis LLP

(57) ABSTRACT

Guiding tube, in particular a trocar, for receiving and guiding a medical instrument, wherein the guiding tube includes engaging members for engaging an instrument inside the tube and a substantially spherically shaped ball member provided on an outer surface of said tube, wherein the engaging members are provided movable with respect to the tube in a direction having a radial component, seen with respect to the longitudinal axis of the tube, upon compression of the ball member.

27 Claims, 15 Drawing Sheets

(51) Int. Cl.
*A61B 17/00* (2006.01)
*A61B 90/50* (2016.01)

(52) U.S. Cl.
CPC ....... *A61B 90/50* (2016.02); *A61B 2017/0042* (2013.01); *A61B 2017/0046* (2013.01); *A61B 2017/347* (2013.01)

(58) Field of Classification Search
CPC ............ A61B 17/3421; A61B 17/3423; A61B 17/3431; A61B 17/3462; A61B 2017/3405; A61B 2017/3425; A61B 2017/3427; A61B 2017/3429; A61B 2017/3445; A61B 2017/3466
See application file for complete search history.

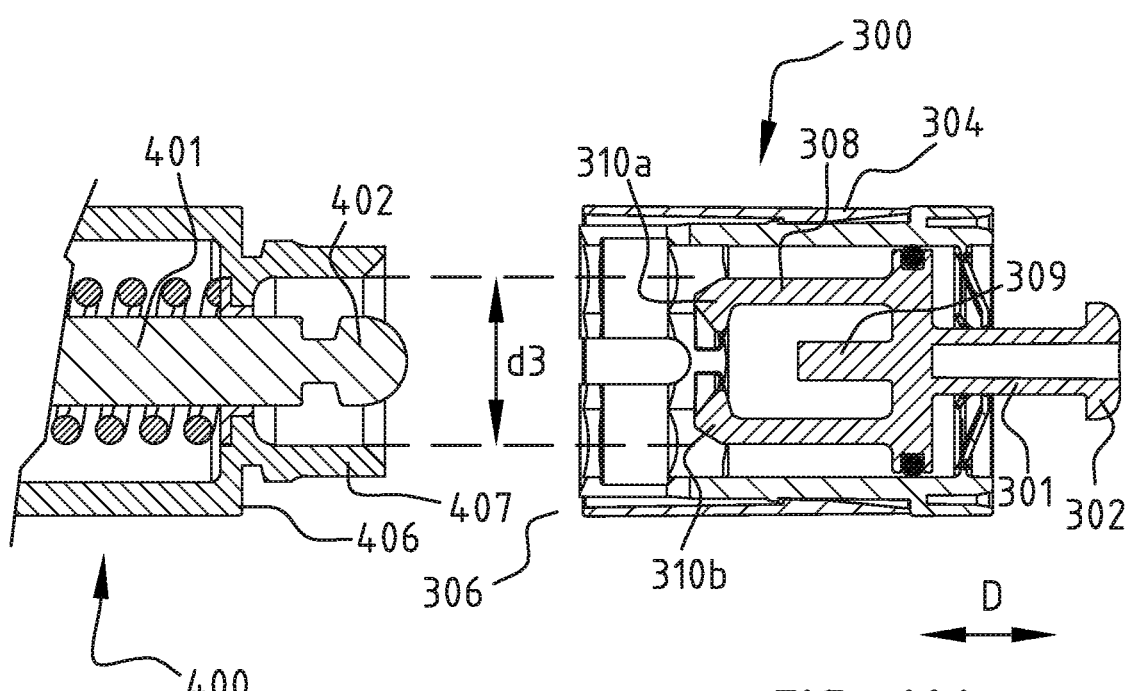
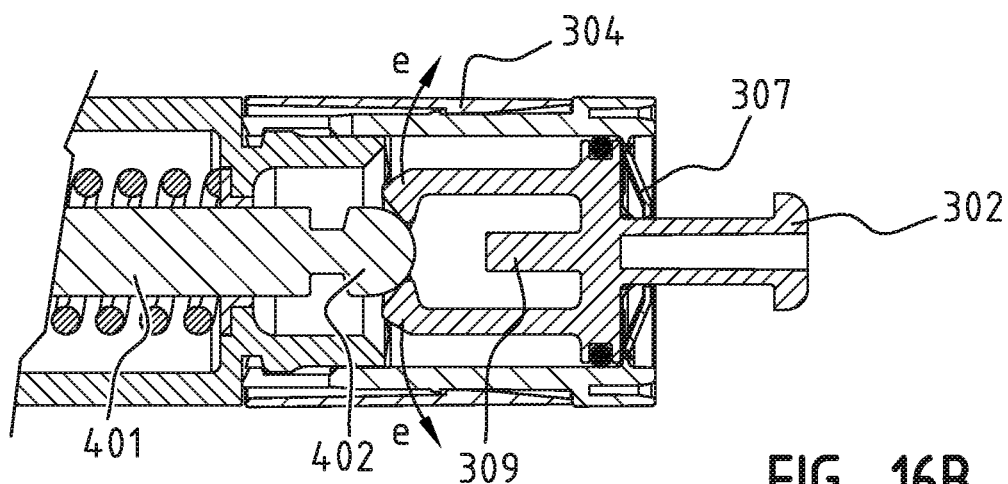

GUIDING TROCAR AND SYSTEM FOR CONNECTING TO A GUIDING TROCAR

The present invention relates to a guiding tube, in particular a trocar, and a holding system for holding the guiding tube comprising a joint device for connecting to a guiding tube, a cover device and a driving device for cooperating with a guiding tube.

During minimally invasive or laparoscopic surgery, medical instruments are introduced into the patient via a guiding tube or trocar. A distal end of a trocar is hereto inserted into a patient, such that instruments can be guiding into the patient via the proximal end of the tube.

It is a goal, amongst other goals, of the present invention to provide an improved guiding tube and/or associated holding system wherein the chance of harm due to unintended movement of the trocar in use is minimized, while still optimal flexibility is provided to the user in positioning and reorienting the guiding tube if needed.

This goal, amongst other goals, is met by a guiding tube according to claim 1. More specifically, this goal, amongst other goals, is met by a guiding tube, in particular a trocar, for receiving and guiding a medical instrument, wherein the guiding tube comprises engaging members for engaging an instrument inside the tube and a substantially spherically shaped ball member provided on an outer surface of said tube, wherein the engaging members are provided movable with respect to the tube in a direction having a radial component, seen with respect to the longitudinal axis of the tube, upon compression of the ball member. Compression, i.e. a force directed in a radially inwardly direction, will then result in engagement, and thereby locking, of an instrument held in the guiding tube. The ball member preferably has a substantially spherical outer surface, such that this surface can function as a bearing surface in a ball joint. The guiding tube is preferably arranged to cooperate with a joint device, preferably provided with a clamping ring as will be explained in greater detail below.

The engagement members, for instance in the form of protrusions, are hereby preferably moveable between an engaging position, in which the engaging members engage and are in clamping contact with an instrument held in the guiding tube, and a loose position, wherein the engaging members are moved with respect, or wherein the clamping force is at least substantially reduced on, the instrument, such that the instrument is moveable in the guiding tube, in particular along the longitudinal axis thereof.

In order to allow the compression of the ball member, the ball member preferably comprises a plurality of mutually movable parts. The parts can be manufactured of a relatively rigid and durable material. The parts are preferably moveable from and towards the guiding tube, in particular the longitudinal axis thereof, wherein the parts are arranged to surround the tube. The parts are preferably substantially wedge shaped parts, wherein the wedge shaped parts form the ball member. The outer surfaces of the wedge shaped parts hereby preferably form a substantially spherical surface as explained above.

An efficient clamping of the instrument can be achieved if an engaging member is located at a radially inward end of at least one of the wedge shaped parts. The movement of a part, preferably a wedge shape part as mentioned above, is hereby efficiently conveyed to the engaging member. A further improved engagement of the instrument in the guiding tube is obtained if the inward end of the wedge shape part has a height, seen in the direction of the longitudinal axis of the tube, that is larger than a height of the engaging member, wherein the wedge part comprises a bridge part for connection with the tube at the inward end, wherein the height of the bridge corresponds to the height of the engaging member. The difference in height of the bridge member and the inner end of the wedge shaped part preferably results in a gap between the wedge shaped part and the tube. Preferably, the bridge part is centred, seen in the direction of the longitudinal axis of the tube, with respect to the wedge shaped part, such that preferably two gaps are formed at the upper and lower part of the inward end.

An guiding tube, in particular a ball member thereof, which is easy to manufacture is obtained if a wedge shaped part comprises two side walls under angle with respect to each other, the side walls being shaped as a circular segment having an inner edge and an arc shaped outer edge, wherein the arc shaped outer edges define the substantially spherical surface of the ball member. Such a wedge shaped part, or a ball member formed of a plurality of these wedge shaped parts, can be efficiently manufactured by injection moulding.

In order to increase the rigidity of a wedge shaped part, it is preferred if two side walls in a wedge shaped part are interconnected by an arc shaped connecting rib at the equatorial plane of the ball. The connecting rib preferably partly defines the spherical outer surface of the ball member. In order to facilitate the movement of the ball member in a joint device, in particular to prevent difficulties in movement between a ring shaped member wherein the ball member is held in a joint device and said ball member, it is preferred the connecting rib is countersunk with respect to the arc shaped outer edges of the side walls. This ensures in a smooth transition from the arc shaped outer ends of the wedge shaped parts to the connecting rib upon rotation of the guiding tube provided with the ball member.

According to a further preferred embodiment, the radially inward ends of the wedge shaped parts are interconnected and wherein the wedge shaped parts extend at mutual distances with respect to each other at a radially outwardly location. At the outer ends, the wedge shaped parts hereby extend at mutual distances with respect to each other. This facilitates the relative movement of the parts with respect to each other. It is hereby preferred if the wedge shaped parts are interconnected at the guiding tube.

As an alternative, it is possible that the ball member comprises wedge shaped parts of a first relatively stiff material which are interconnected by a relatively flexible second material, wherein the first and second materials together form the ball member. This provides a smooth and substantially continuous spherical surface, which facilitates rotating of the ball member.

According to a further preferred embodiment, the engaging members are formed integrally on an inner surface of the tube, wherein the tube has a non-circular cross-section at at least the location of the engaging members. This cross-section facilitates movement of the engagement member, as a tube having a circular cross-section is difficult to deform. It is hereby preferred if the tube has a varying radius seen along the perimeter, defining wall sections having larger radii and wall sections having smaller radii. Seen along the perimeter of the guiding tube, the diameter thus varies, resulting in a corrugated wall. This provides flexibility to the wall of the guiding tube, thereby facilitating movement of the engaging members provided on the wall. To improve the clamping action, it is preferred the engaging members are located on either the wall sections having the larger radii or the wall sections having the smaller radii. An even further improved clamping action is obtained if the engaging members are located on the wall sections having the larger radii.

An efficient tube which allows efficient movement of the engagement members provided on the guiding tube is provided when the tube has a substantially polygonal cross-section, preferably triangular, wherein the edges are arc shaped and wherein the engaging members are located at midpoints of said edges. The midpoints of said edges are then relatively easy to move, in particular in comparison to a circular cross-section, upon compression of the ball member.

An efficient and compact composition is obtained if the ball member is formed integrally with the guiding tube. The guiding tube is hereby provided in one piece, wherein preferably also the engaging members are formed integrally with, or are at least connected to, the ball member and the guiding tube. The engaging members being integral with the ball member, in particular the ball member having the plurality of wedge shaped parts, further improves the movement of the engaging members in reaction to compression of the ball member, thereby improving the clamping action.

According to an alternative embodiment, the ball member is formed as a separate piece. This allows adjustment of the ball member to the guiding tube, for instance in terms of location of the ball member and the guiding tube. It is for instance possible that the ball member is arranged in a sliding manner on the guiding tube, such the height, seen in the direction of the longitudinal axis of the guiding tube, can be adjusted. This allows moving of the pivot point, such that the pivot point can be placed as close as possible to the patient in use, independent of the insertion depth of the guiding tube. It is hereby preferred if the ball member is provided with a through hole substantially corresponding to the outer shape of the tube. In case the tube has a non-circular cross-section, rotation around the longitudinal axis is also prevented.

It is hereby possible that the engaging members are formed integrally with the ball member. In order to allow clamping of an instrument in the guiding tube, said tube is preferably provided with corresponding through holes for receiving the engaging members, for instance in the form of protrusions as mentioned above. In order to allow the movement of the ball member with respect to the guiding tube, it is preferred if the holes are slit shaped in the direction of the longitudinal axis of the tube, such that the ball member with engaging member can be moved along said longitudinal axis with respect to the tube.

As an alternative, the engaging members are formed integrally with the guiding tube. This ensures a closed wall of the guiding tube. In order to allow movement of the ball member with respect to the guiding tube, it is hereby preferred if the engaging members extend along a length, seen in the direction of the longitudinal axis of the guiding tube, of said guiding tube, such that ball member can be moved, while still ensuring cooperation of the ball member and the engaging members. Preferably, the engaging members extend along a length which is larger than the height of the ball member.

It is also possible that the engaging members are formed by the inner surface of the guiding tube. In this embodiment, the engaging members do not protrude from the inner wall of the guiding tube. Compression of the guiding tube due to compression of the ball member will hereby result in the inner wall of the guiding tube engaging the instrument, thereby preventing movement thereof.

A further preferred embodiment of the guiding tube according to the invention further comprises an adapter tube inserted into the guiding tube, the adapter tube having an outer diameter substantially corresponding with the inner diameter of the guiding tube, wherein at least a part of the wall of the adapter tube at the location of the engaging members is moveable for engaging an instrument. This allows the guiding tube to be used with a greater variety of instruments with varying diameters, as the adapter tube will compensate for the difference in diameter. As at least a part of the wall of the adapter tube is moveable, the engaging members will force the part of the wall to the inside to clamp the instrument if needed. Preferably, the adapter tube comprises a plurality of slits at one end, wherein the moveable wall parts are formed there between.

The invention further relates to a joint device for holding a guiding tube, preferably a guiding tube according to the invention, wherein the joint device comprises a clamping member arranged for engaging a ball member of the guiding tube, wherein the clamping member is moveable between a locked position wherein the ball member is firmly clamped for locking movement of the ball member with respect to the clamping member and a movable position, wherein the ball member is movable with respect to the clamping member for rotating the guiding tube. The ball member of the guiding tube is hereby used as a bearing surface to create a ball joint. This allows rotation of an instrument held in the guiding tube, more specifically rotation along two rotation axes perpendicular to the longitudinal axis of the guiding tube and thereby of the instrument.

The clamping member is arranged to exert a firm clamping action on the ball member in the locked position, such that the ball member is fixed in terms of position with respect to the joint device. It is preferred that in this position, the instrument held in the guiding tube is also prevented to move due to the engagement of the engaging members as described above. The clamping member thus preferably locks the ball member with respect to the joint device and the instrument with respect to the ball member, and thus the guiding tube. In the movable position, the ball member is held sufficiently loose such that the ball member is allowed to rotate in the clamping member.

According to a preferred embodiment, the clamping member comprises a substantially loop or ring shaped element having an inner diameter substantially corresponding to the outer diameter of the ball member, wherein the inner diameter is adjustable for moving between the movable and locked positions. This allows an efficient movement between the movable and the locked position of the clamping member.

A further improved clamping action is obtained if the joint device comprises a stationary part and wherein the joint device is arranged to clamp the ball member between the stationary part and the clamping member. The ball member is hereby clamped between the clamp member and the stationary part in the locked position.

The stationary part may be formed as a piece of the joint device, for instance the housing thereof. However, according to a further preferred embodiment, the stationary part is formed by an end region of the loop shaped clamping member, wherein the end region of the clamping member is fixed in the joint device and wherein the opposite end of the clamping member is arranged to be moved for moving the clamping member between the positions. The clamping member is hereby preferably tightened, as a loop, around the ball member upon movement of the opposite end. The direction of movement of the opposite end for moving between the positions preferably has a component in the radial direction, seen with respect to preferably ring shaped member. For instance a pulling action on the opposite end then results in an efficient clamping action of the clamping member.

In order to efficiently actuate the clamping member, it is preferred if the clamping member comprises a receptacle for receiving a connecting member of a driving rod of a connected device, for instance a driving device, wherein the driving rod is movable between an extended and a retracted position for moving the clamping member between the positions. The receptacle is then arranged to firmly couple to the connecting member of the driving rod, thereby moving the clamping member between the positions. Preferably, the connecting member comprises a widened end portion of the driving rod and wherein receptacle is arranged to receive said widened end portion of the driving rod. This allows an efficient coupling of the receptacle and the driving rod, while still ensuring a reliable transfer of the movement of the driving rod to the clamping member. The joint device is hereto preferably arranged to move the clamping member in the locked position in the retracted position of the driving rod.

It is hereby noted that the terms retracted position and extended position refer to the positions of the driving rod with respect to the device inducing the movement, for instance a driving device. In the retracted position, the end portion of the driving rod extends at a distance from the for instance the housing of the driving device which is smaller than the position of the end portion in the extended position.

To provide a reliable connection between the joint device and a device to be coupled thereto, for instance a driving device, the joint device preferably comprises an annular rim for connection with a correspondingly shaped rim of a connected device, for instance a driving device. The correspondingly shaped rims than ensure a reliable interconnection.

When a driving rod is moved to the retracted position, that is moved away from the joint device as mentioned above, the cooperating rims of the joint device and connected device will be urged together, thereby ensuring a locked interconnection. If the driving rod is however moved to the extended position, the cooperating rims may be moved apart, such that movement, in particular rotation, of the rims is possible. This allows a further way of adjusting the position of the instrument held in the guiding tube with respect to the connected device, which is preferably connected to the fixed world by for instance a frame member.

Therefore, according to a further preferred embodiment, the receptacle is arranged to receive the driving rod such that the driving rod extends parallel to the central axis of the annular rim and wherein the central axis extends under an angle, preferably perpendicularly, with respect to the central axis of the clamping member, wherein the joint member is arranged to allow rotation around the central axis of the annular rim with respect to the connected device in the extended position of the driving rod. This provides extra flexibility in adjusting the position and orientation of the guiding tube, and thereby the instrument held therein.

An even more reliable connection between two devices in the retracted position of the driving rod, while allowing rotation in the extended position of the driving rod is obtained if one of the rims of the joint device or the connected device has a tapered end, and wherein the rim of the other of the joint device or the connected device has a correspondingly shaped end. As an alternative, or in addition thereto, the rims of the joint device and the connected device are provided with cooperating toothing. When the devices are moved apart, for instance by extending the driving rod, the teeth of the devices are moved apart, thereby allowing relative movement. If the devices are pulled together by retracting the driving rod, the teeth will engage, thereby preventing relative rotation.

In order to improve the clamping action of the clamping member on the ball member, it is preferred if the clamping member comprises a contacting surface arranged for contacting the ball member, wherein the contacting surface is provided with at least one protrusion or a plurality of protrusions for engaging the ball member along at least a part of the circumference of the ball member. The protrusion may for instance be arranged to locally (elastically) deform the ball member, thereby creating an improved locking interconnection of the protrusion in the deformed ball member. An efficient clamping member is hereby obtained if the clamping member comprises a flange, preferably two flanges, for engaging the ball member along the circumference of the ball member.

A guiding tube and associated joint device are typically used in surgery, such that a sterile environment is necessary. Providing a driving device, typically provided with a motor, to induce the movement of for instance the driving rod as described, which is sterile and which can be sterilized is however difficult. Therefore, according to a further preferred embodiment, joint device further comprises a tubular covering sleeve for covering a connected device, such as a driving device, wherein one end of the sleeve is closed and sealed to the joint device and wherein the other end is open so as to cover the connected device and possibly other equipment such as a holding frame. The sleeve is used to cover all the components, such as the driving device and the frame connected thereto, such that these components do not need to be sterilized. Only the components distal to the sleeve need to be sterilized.

Although it is possible to provide the joint device with the covering sleeve, it is preferred if a sleeve, as a disposable part, is not connected to the joint part. The invention therefore further relates to a cover device arranged to be connected between a joint device, preferably according to the invention, and a driving device and which is arranged to transfer the movement of a driving rod from the driving device to the joint device, wherein the cover member comprising a tubular covering sleeve for covering a connected device, such as the driving device, wherein one end of the sleeve is closed and sealed to the cover device and wherein the other end is open so as to cover the connected device and possibly other equipment such as a holding frame.

In order to be able to convey or transfer the movement of the driving rod, the cover device according to a preferred embodiment comprises a transfer member which is movable with respect to the cover device for transferring the movement of the driving rod of the driving device in connected state, wherein a first end of the transfer member is arranged for receiving a connecting member, for instance a widened end portion, of the driving rod and wherein the opposite second end comprises a connecting member for connecting to the joint member, wherein said connecting member is movable between a retracted and extended position with respect to the cover device.

Preferably, the first end of the transfer member comprises mutually movable hook shaped members for engaging the connecting member, wherein the hook shaped members are movable between a insertion position wherein the hook shaped members are at a distance allowing the connecting member to pass, and a engaged position wherein the hook shaped members engage the driving rod behind the connecting member. This allows a reliable and efficient interconnection of the transfer member and the driving rod. The hook shaped members are preferably sufficiently resilient such that upon insertion of the driving rod, the hooks are urged apart by the widened portion. As the driving rod has a smaller diameter more proximal to the widened portion, the hooks will snap back to their original position, i.e. engaged position, when the widened portion has passed. This ensures a reliable interconnection.

To prevent accidental and unintentional loosening of the cover device, it is preferred if the cover device further comprises locking means for locking the hook shaped members in the engaged position. The locking means may for instance prevent movement of the hooks. It is hereby preferred if the locking means are positioned for locking the hook shaped members in the retracted position of the driving rod. This retracted position preferably corresponds to the locked position of the clamping member, and therefore of the engaging members as mentioned above. An efficient locking is achieved if the locking means comprise an annular rim for receiving the hook shaped members in the retracted position for limiting outwardly movement of said hook shaped members. It is hereby possible that the annular rim is provided in the cover device at and end towards the first end of the transfer member. Upon retraction of the driving rod, the hooks are received in the correspondingly shaped rim, thereby preventing bending of the hooks.

It is however also possible that the rim is provided on the device to be connected to the cover device. The invention therefore also relates to a combination of a driving device comprising a driving rod which is moveable between a retracted and an extended position and a cover member according to the invention, wherein the cover device is arranged such that the driving rod of the driving device is connectable to first end of the transfer member in the extended position of the connecting member of the transfer member. The annular rim may hereby be provided on the driving device.

According to a preferred embodiment, the driving device and cover device comprise cooperating contact surfaces for contacting each other in the connected stage, wherein the cover device and the driving device are arranged such that the connecting member of the driving rod is in engagement with the first end of the transfer member in connected state. This allows efficient transfer of the movement of the driving rod of the driving device, via the transfer member of the cover member, to for instance the joint member as mentioned above.

The invention furthermore relates to a driving device, preferably for use with the joint device or cover member according to invention, wherein the driving device comprising a housing and a driving rod provided with a connecting member at its end, wherein the driving device is further provided with moving means for moving the driving rod between an extended position and a retracted position, both with respect to the housing. The driving device is preferably provided with suitable connection means for connecting the driving device to a supporting frame.

In order to automatically move a connected joint device to the locked position, thereby preferably also locking an instrument held in a guiding tube according to the invention, the driving device preferably comprises biasing means for biasing the driving rod towards the retracted position. Preferably, the biasing means comprise a spring mounted between a housing part and a flange part of the driving rod for biasing the driving rod into the retracted position. The spring then urges the flange, and thereby the driving rod, away from the end of the housing, i.e. to the retracted or locked position.

It is preferred if the driving rod can be moved manually to the extended position, i.e. movement out of the housing. Manual movement is often preferred over motorized movement by users due to the speed and ease of handling. According to a further preferred embodiment, the moving means therefore comprise a handle for moving the driving rod to the extended position. A reliable and simple design is obtained if the handle is formed as a lever for urging the driving rod towards the housing part. It is hereby preferred if the lever engages the flange part of the driving rod onto which the biasing means engage.

According to a further preferred embodiment, the driving means comprise a motor for moving the driving rod, wherein the driving device further comprises a controller for controlling the motor. This improves the user-friendliness of the device. It is however preferred if both the handle and the motor are arranged for moving the driving rod. Both the handle and the motor may for instance engage the flange part of the driving rod for moving said rod.

According to a further preferred embodiment, the motor comprises a rotation motor, wherein the rotation axis of the axle of the rotation motor is substantially parallel to longitudinal axis of the driving rod. For providing a translating movement in the longitudinal direction of the driving rod, the axle preferably extends in a driving bushing operably connected to the driving rod, wherein the inner surface of the bushing and the axle are provided with cooperating threading for translating the driving bushing upon rotation of the axle for moving the driving rod.

To prevent damage to the driving device, the driving device preferably further comprises rotation limiting means, wherein the rotation limiting means more preferably comprise a pin connected to the axle which is movable between two engaging surfaces provided on the driving device, for instance on an inner surface of the housing.

A further preferred embodiment comprises storage means operable coupled to the controller for storing driving device data, such as a unique identification number and device usage history, including motor operation. Statistics of the device are then readily available.

In order to be able to remotely control the motor, for instance from the location of the instrument, to preferred embodiment of the driving device further comprises a connector for connecting the controller with an external actuator for controlling the motor.

The present invention is further illustrated by the following Figures, which show preferred embodiments of devices according to the invention, and are not intended to limit the scope of the invention in any way, wherein.

Figure 9:
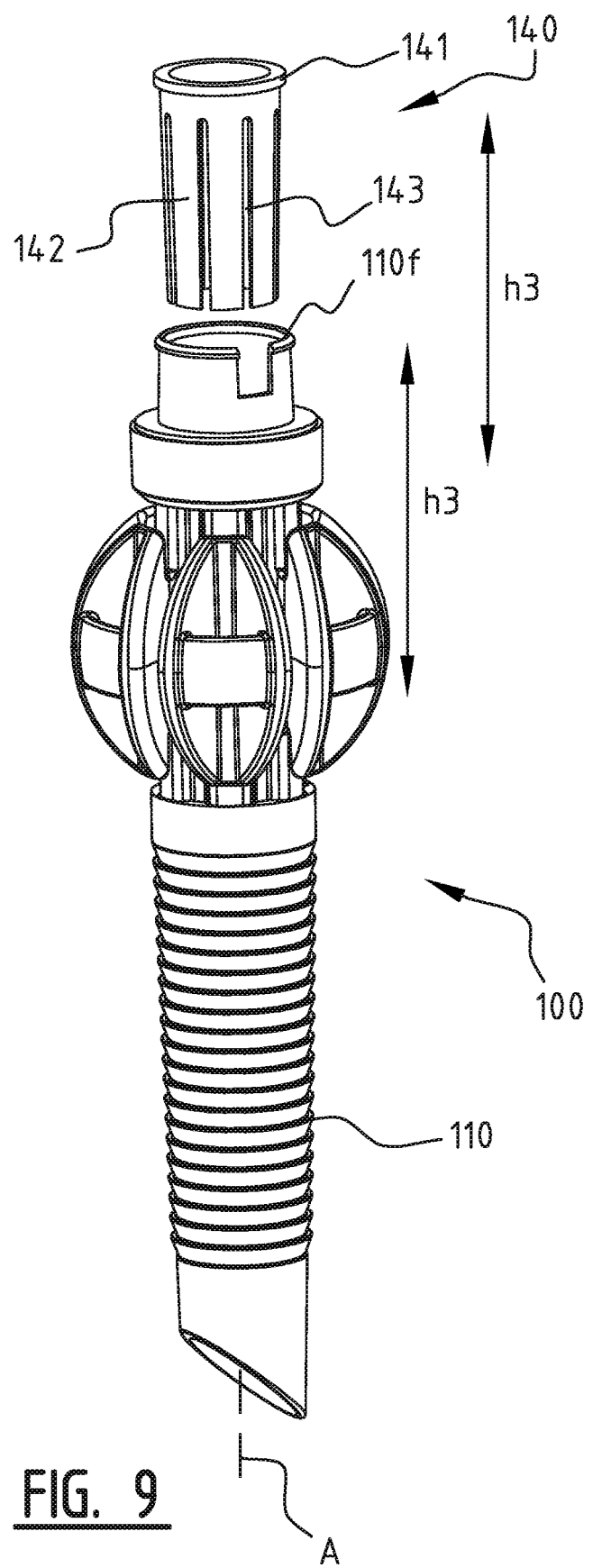
Figure 10:
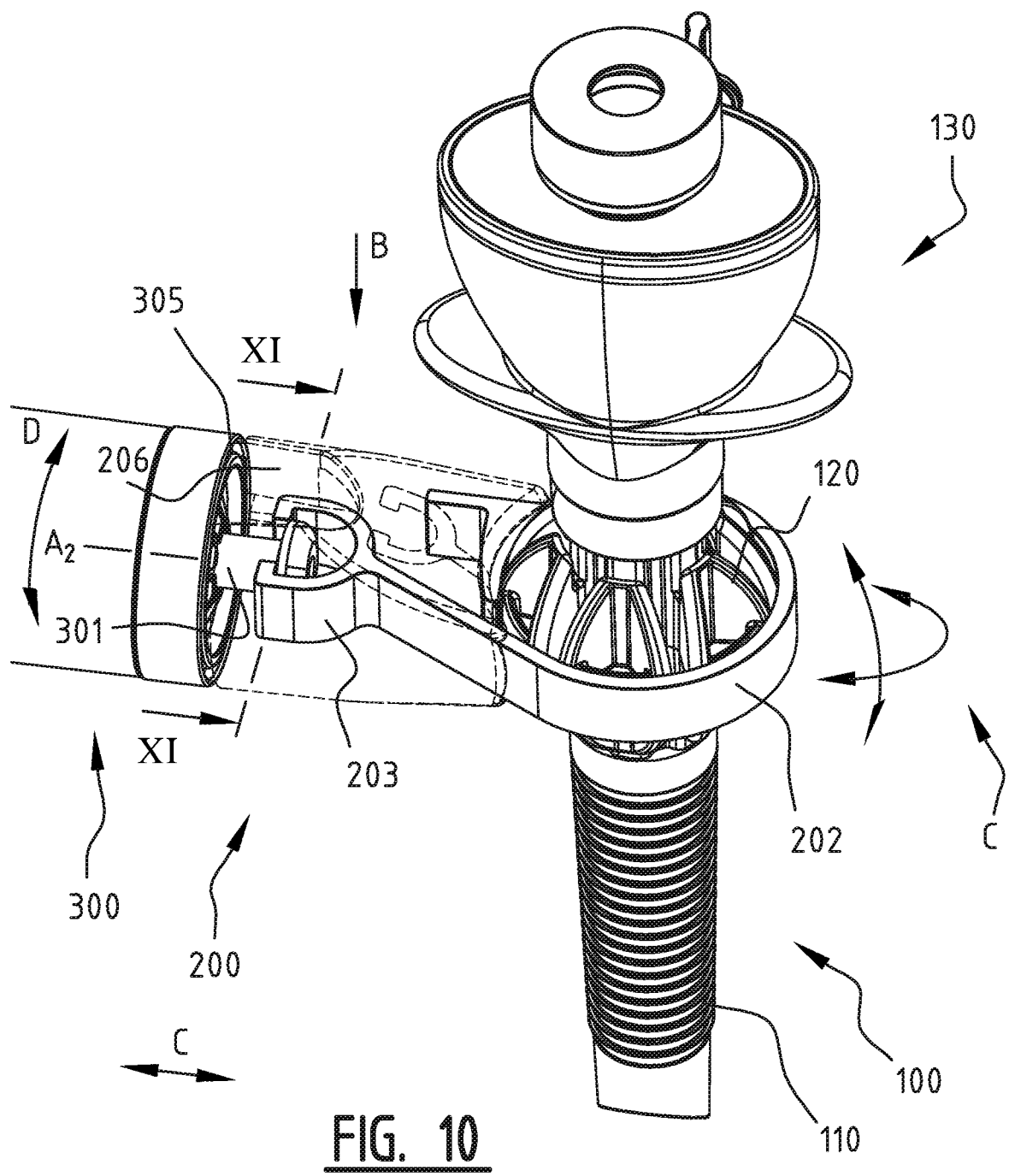
Figure 11:
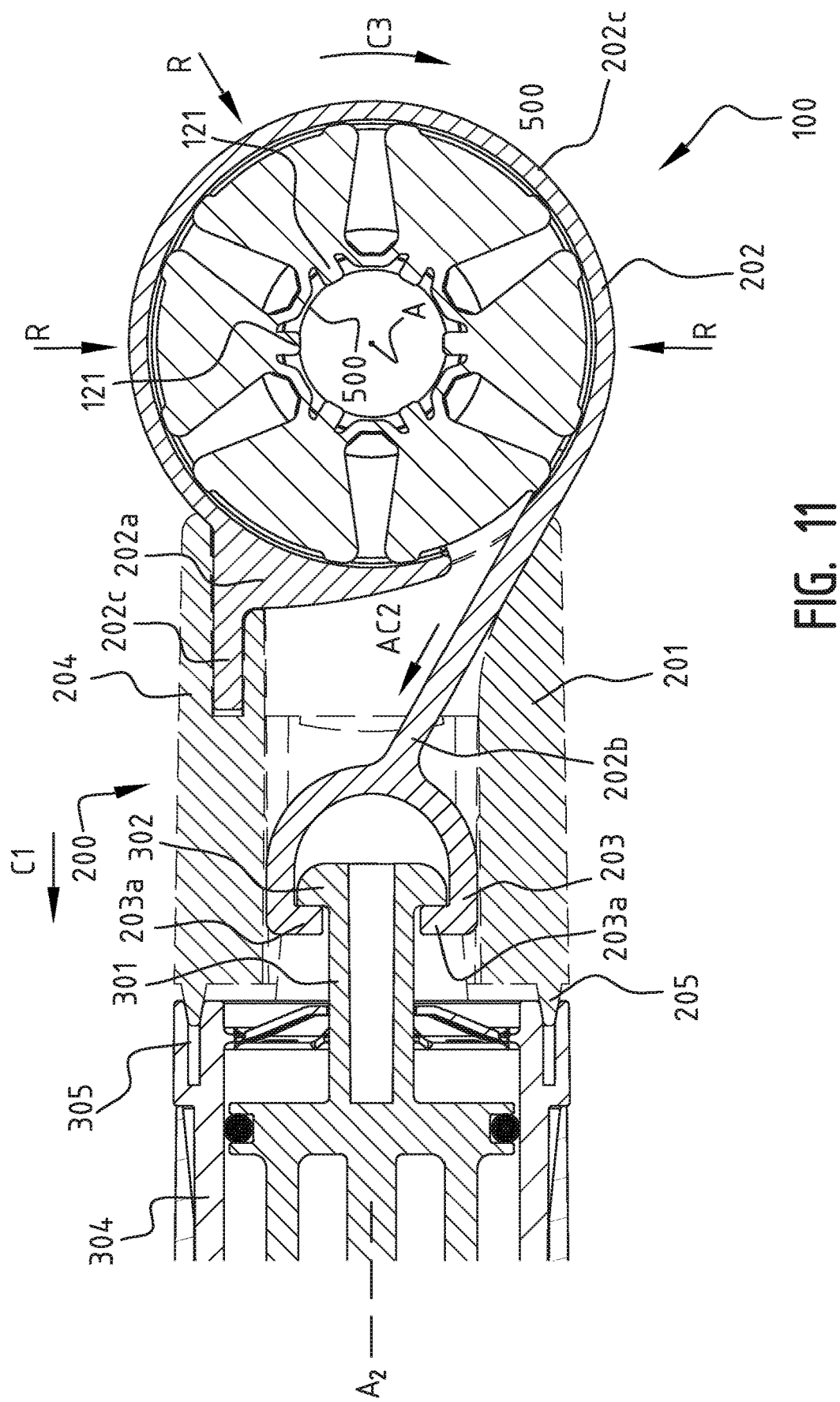
Figures 12A, 12B:
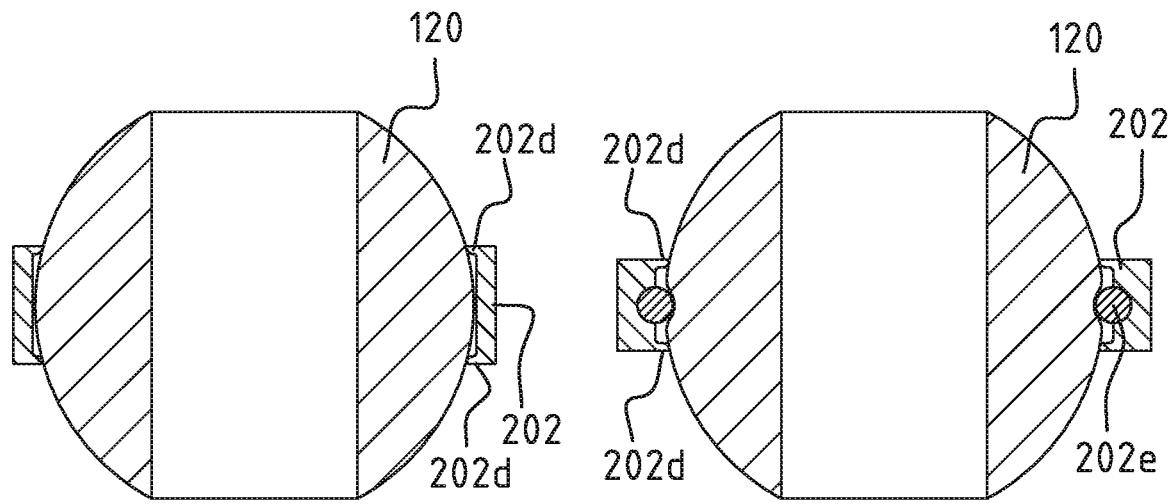
Figure 13:
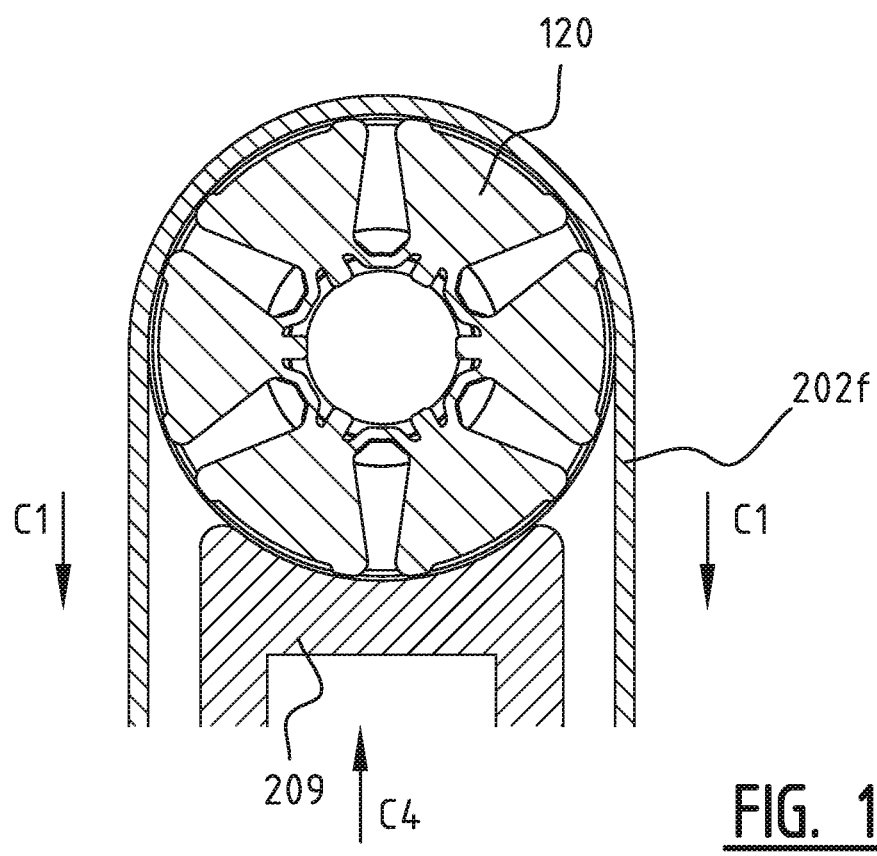
Figure 14:
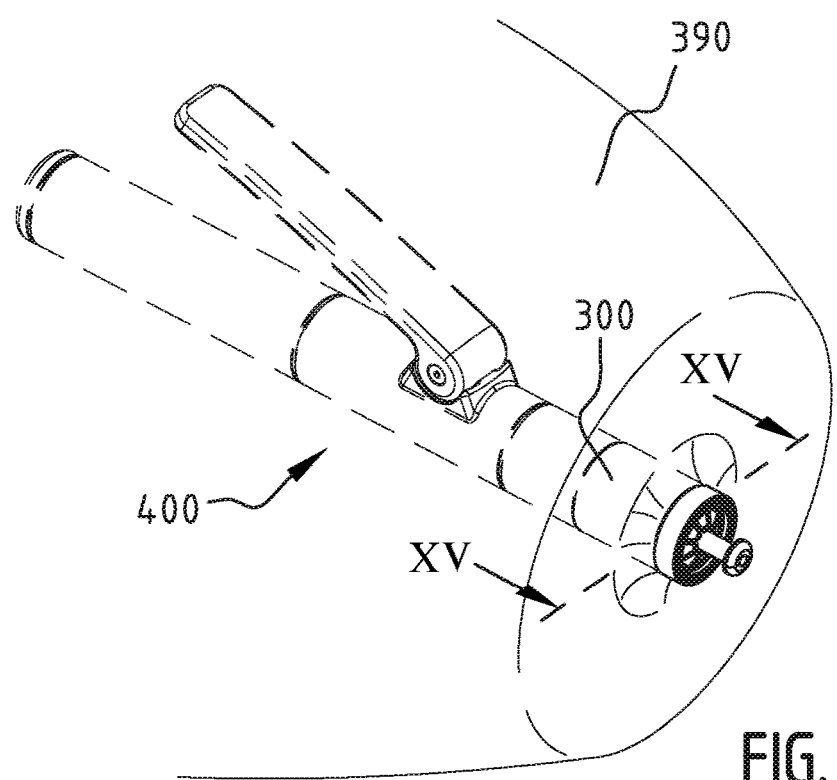
Figure 15:
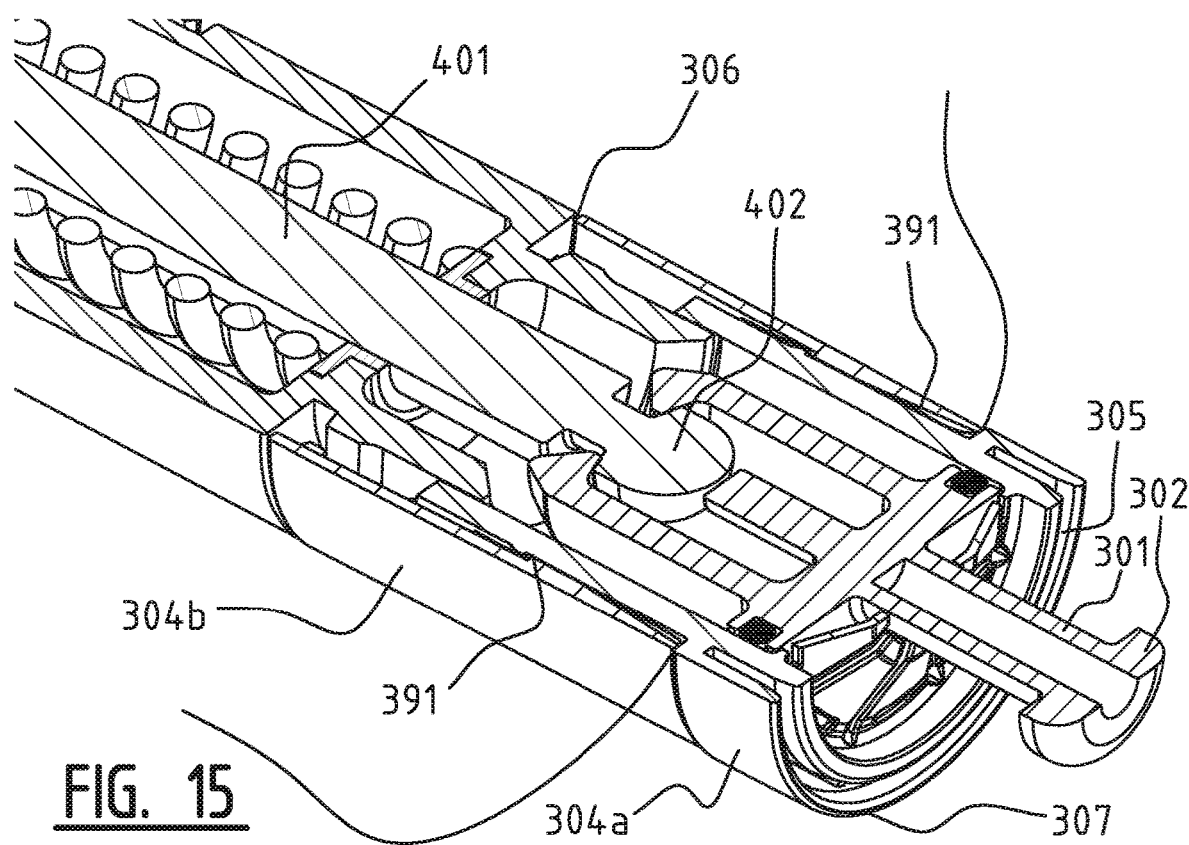
Figure 17:
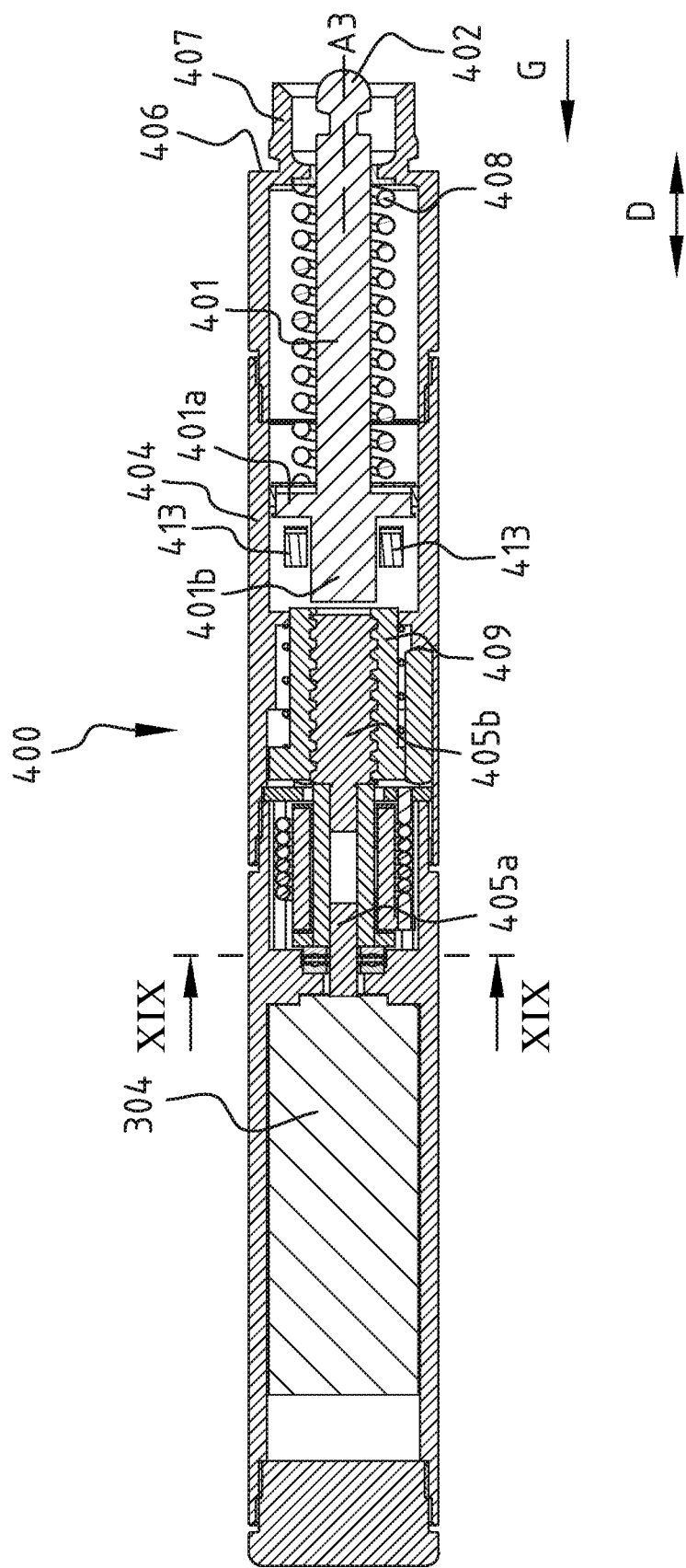
Figures 18, 19:
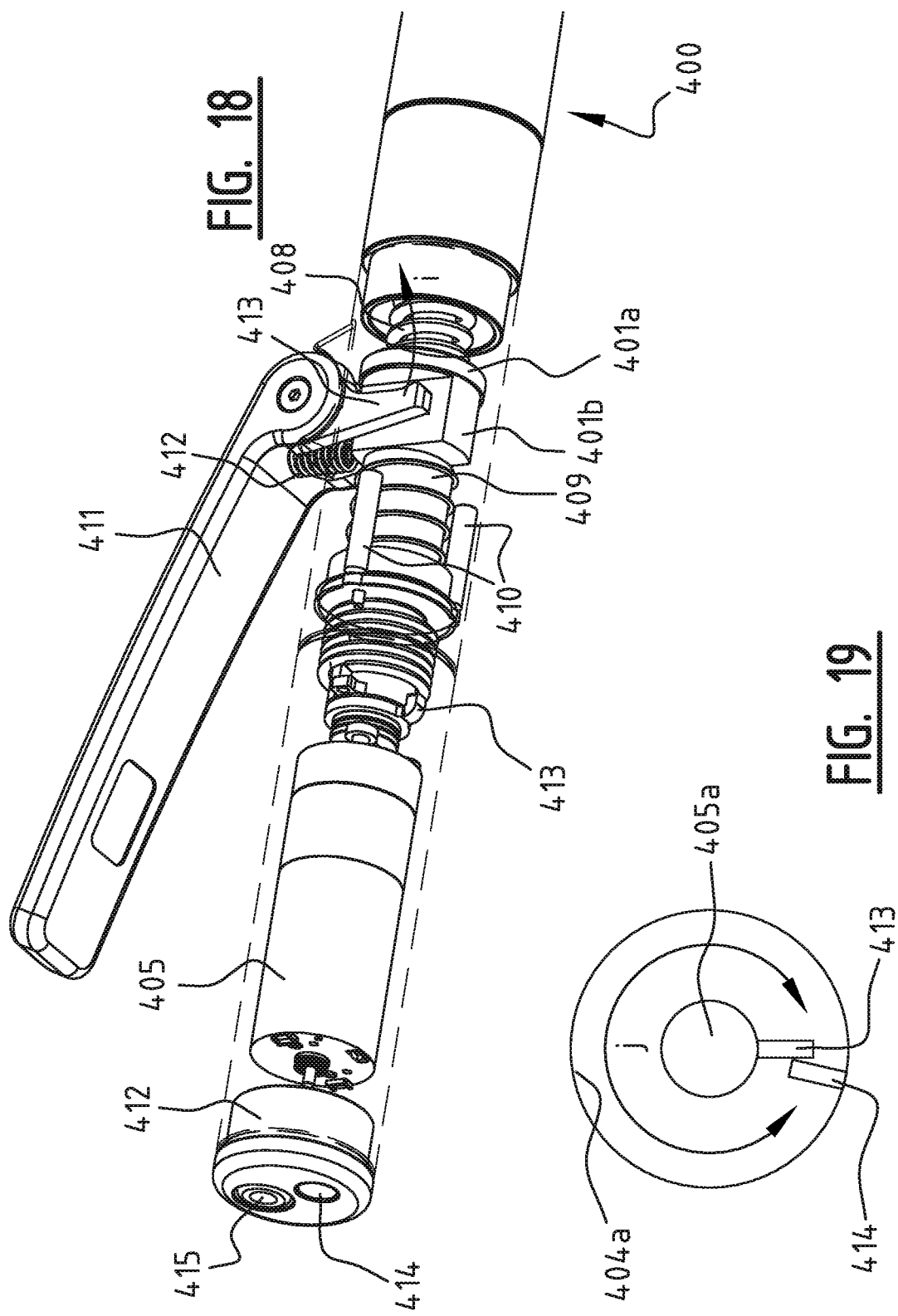

FIG. 9 schematically shows an adapter for the trocar;

FIG. 10 schematically shows a joint device for holding a trocar;

FIG. 11 shows the joint device with a trocar in cross-section;

FIGS. 12a and 12b schematically show the clamping member for clamping the ball member of a trocar;

FIG. 13 shows a cross-section of an alternative clamping member;

FIG. 14 schematically shows a tubular sleeve for covering the driving device and support frame of the holding system;

FIG. 15 shows a cover device in cross-section;

FIGS. 16a-d schematically show the process of coupling a driving device to the cover device;

FIG. 17 schematically shows the driving device in cross-section;

FIG. 18 schematically shows the interior of the driving device in perspective; and FIG. 19 shows a cross-section of the driving device perpendicular to the longitudinal axis.

Figure 1:
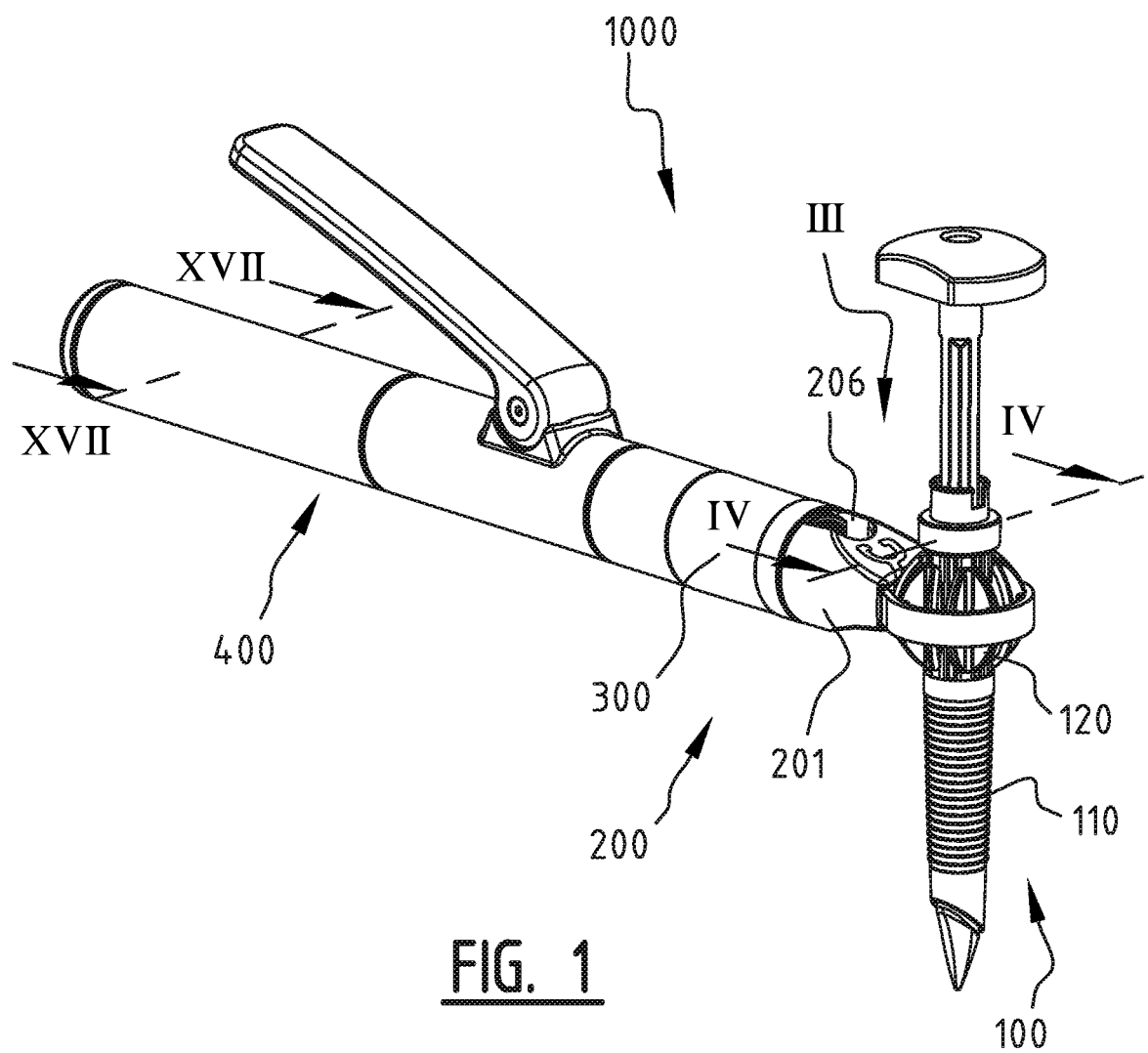
FIG. 1 shows an overview of the holding system with the trocar in perspective.

In FIG. 1, an overview of a trocar holding system 1000 is shown. This system is arranged to hold a trocar 100 by use of a joint device 200. This joint device 200 is coupled via a cover device 300 to a driving device 400.

Figure 2:
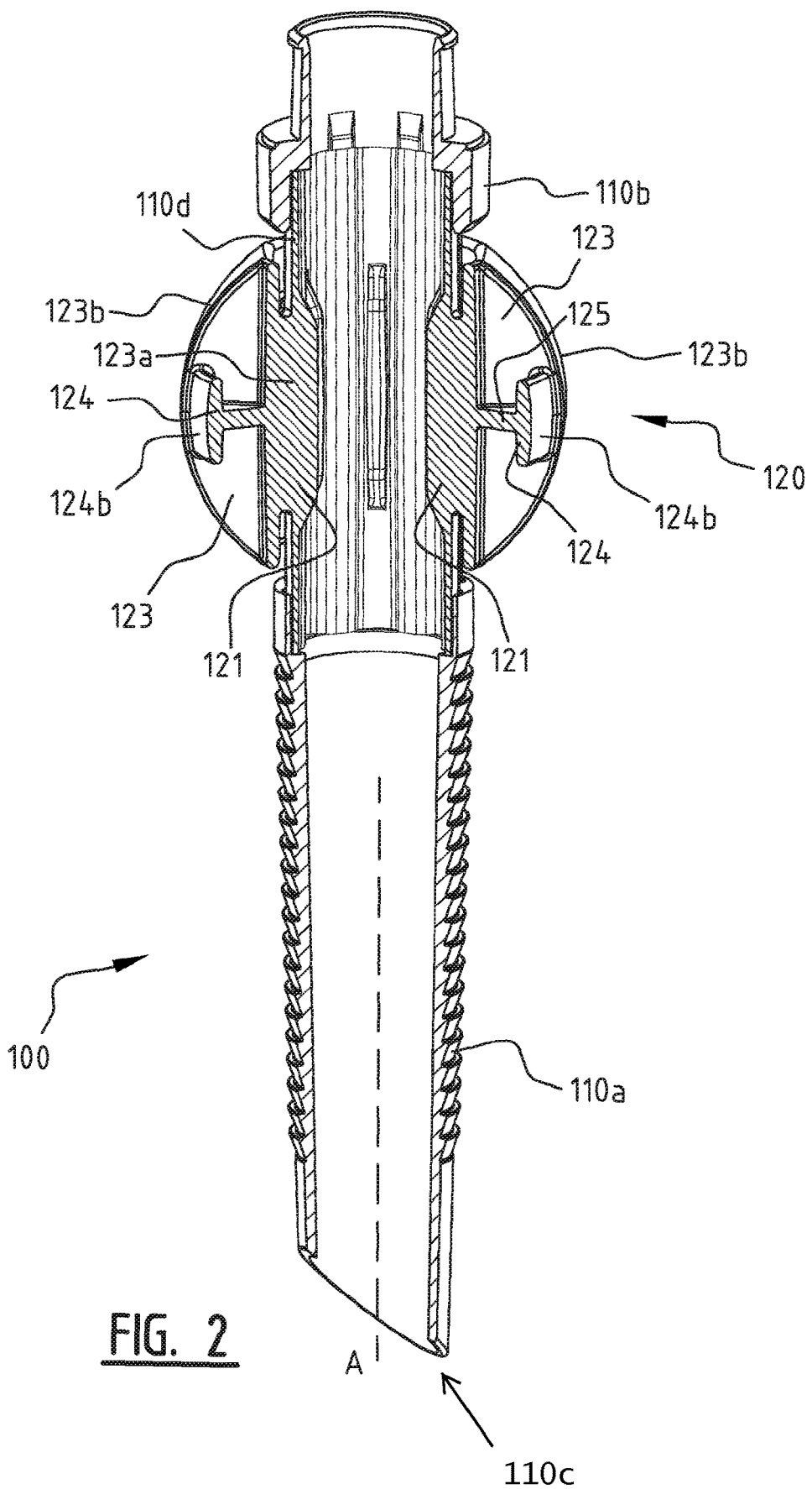
FIG. 2 shows the interior of the trocar.

With further reference to FIG. 2, the trocar 100 comprises a tubular member 110 on which a ball member 120 is provided. The ball member 120 is designed to cooperate with the joint member 200 to form a rotation joint as will be explained in greater detail below. The tubular member 110 comprises three two sections 110a, 110b and 110d in this example, which are interconnected by gluing. The ball member 120 is formed integrally with the tube section 110d in this example. On top of the upper tube member 110b, an introducer port may be provided. The introducer port 130 is for instance shown in FIG. 10 and is provided with a seal (not shown) for creating substantially airtight sealing. The lower tube member 110a comprises a corrugated outer surface in this example which provides pull out resistance when inserted into an insertion in the patient. For easy introduction, the distal end 110c is slanted with respect to the longitudinal axis A of the trocar 100.

The inner surfaces of the tubular sections 110a, 110b and 110d form a substantially smooth passage for an instrument. In order to lock the instrument in the trocar, more specifically to prevent any movement of an instrument along the longitudinal axis A of the trocar 100, engaging members 121 are provided which extend in the passage of the trocar 100, see also FIGS. 3 and 4. The trocar 100, and in particular the ball member 120 and the associated tube section 110d thereof, is designed such that the engaging members 121 are movable in the radial direction R to and from the longitudinal axis A of the trocar, which is indicated with the arrows R in FIGS. 3 and 4. Movement of the engaging members 121 towards the longitudinal axis A will result in the engaging members 121 to engage an instrument 500 held in the trocar 100, thereby preventing movement of the instrument 500.

The part of the trocar 100 formed by the tube section 110d and the ball member 120 is made of a relatively stiff material, in this example plastic. In order to provide sufficient flexibility to allow the engaging members 121 to move inwardly and outwardly, the tube 110d at the location of the engaging members 121 is formed to have a varying radius along the perimeter. The cross-section of the tube 110d in this example is provided with sections 110d1 having larger radii, i.e. a larger distance to the longitudinal axis A, and sections 110d2 having smaller radii, i.e. a smaller distance to the longitudinal axis A. The engaging members 121 are provided on the sections 110d1 with the larger radii.

Figure 7:
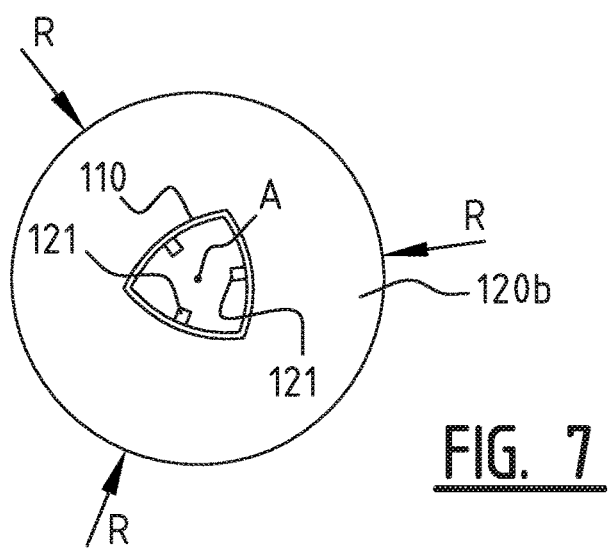
FIG. 7 is a cross-section of the trocar of FIG. 6.

As an alternative, with reference to FIG. 7 which will be explained in greater detail below, the cross-section of the tube 110 may be substantially triangular, wherein the edges of the triangular cross-section are arc shaped and are curved in a direction away from the longitudinal axis A. The engaging members 121 are provided on the midpoints of the edges. Also in this example, the non-circular cross-section provides sufficient flexibility to allow the engaging members 121 to move radially with respect to the longitudinal axis A to engage and clamp an instrument in said trocar.

Figure 3:
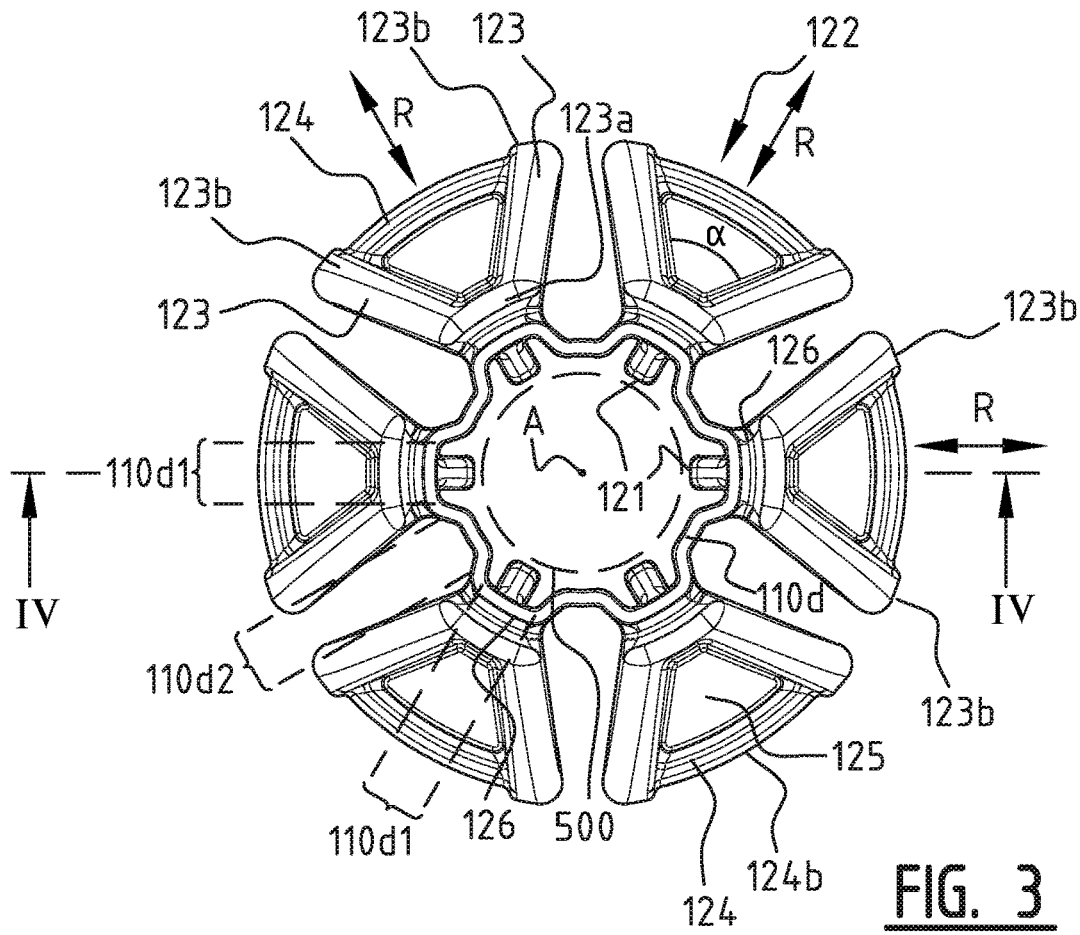
FIG. 3 is a top view of the ball member of the trocar.

Back to FIGS. 1 and 3, it can be seen that the ball member 120 is formed by six wedge shaped parts 122, the outer surface of which together for a substantially spherical surface. A wedge shaped part 122 is formed by two side walls 123 which are interconnected at their radially inward ends or edges 123a. At this location, an engaging member 121 is provided. Two side walls 123 extend under an angle α with respect to each other, thereby forming a spherical wedge shape. The side walls 123 have the shape of a semi disk, of which the outer edges 123b, i.e. away from the tube 110d or the longitudinal axis A, are arc shaped for forming the substantially spherical surface. The two side walls 123 of a wedge part 121 are interconnected by an arc shaped rib 124, which is provided on the equatorial plane of the ball member, see for instance FIGS. 2 and 4. The rib 124 is arc shaped to form along the outer surface 124b a substantially spherical surface. The ribs 124 are however countersunk with respect to the outer edges 123b of the side walls 123, at least at the interconnection of the rib 124 and the side walls 123. This ensures that a ring shaped clamping member, as will be explained in greater detail below, can move freely over the spherical surface, without hitting an edge of the ribs 124. The outer surface 124b of the ribs 124 therefore extend along a spherical surface, preferably substantially along, albeit countersunk with respect to, the same surface along which the outer edges 123b of the side walls 123 extend. For further support, an annular disc 125 is provided which connects the rib 124 to the side walls 123.

As the wedge shape parts 122 extend at a mutual distance, the relatively stiff subunits of the wedge parts 122 can move relatively to each other, i.e. to and away from the longitudinal axis A. As mentioned above, this movement is further facilitated by the flexible interconnection of the wedge shaped parts 122 by the wall sections having the varying radii. Compressions of the ball member 120, i.e. movement of the wedge shaped parts 122 towards the longitudinal axis A, will thus result in a movement of the engaging members 121 towards the axis A.

Figure 4:
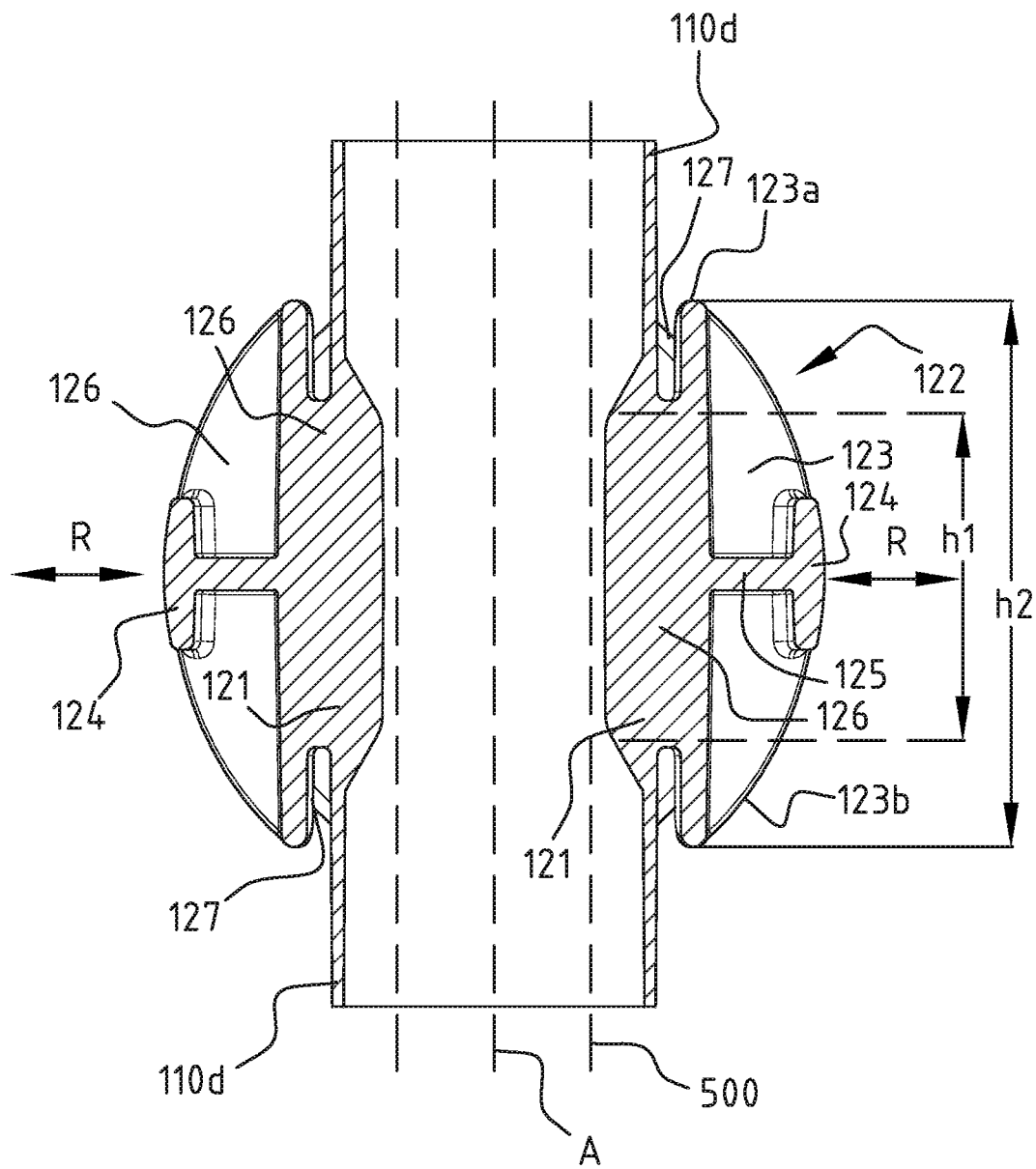
FIG. 4 is a cross-section of the ball member of the trocar.

The interrelation of the engaging members 121 with respect to the wedge shape parts 122 is shown in greater detail in FIG. 4 which shows a cross-section along the median plane of a wedge shape part along line IV-IV in FIG. 3. As descried above, the side walls 123 are interconnected at their inner edges 123a. In this example, the ball member 120 is formed integrally with the tube, such that the inner edges 123a are connected to the tube. The wedge parts 122 are connected with bridges 126 to the tube 110d, wherein the engaging members 11 are aligned with said bridges 126. The height h2 of the bridges hereby substantially corresponds to the height of the engaging members 121, such that any compression exerted on the spherical surface of the ball member 120 is efficiently transferred to the engaging members 121. From FIG. 4 it follows that the height h1 of the inner edges 123a is larger than the height h1 of the bridges 126, such that a gap 127 is created between the upper and lower parts of the inner edges 123a. This further facilitates the transfer of any compression force on the ball member to the engaging members 121.

Figure 5:
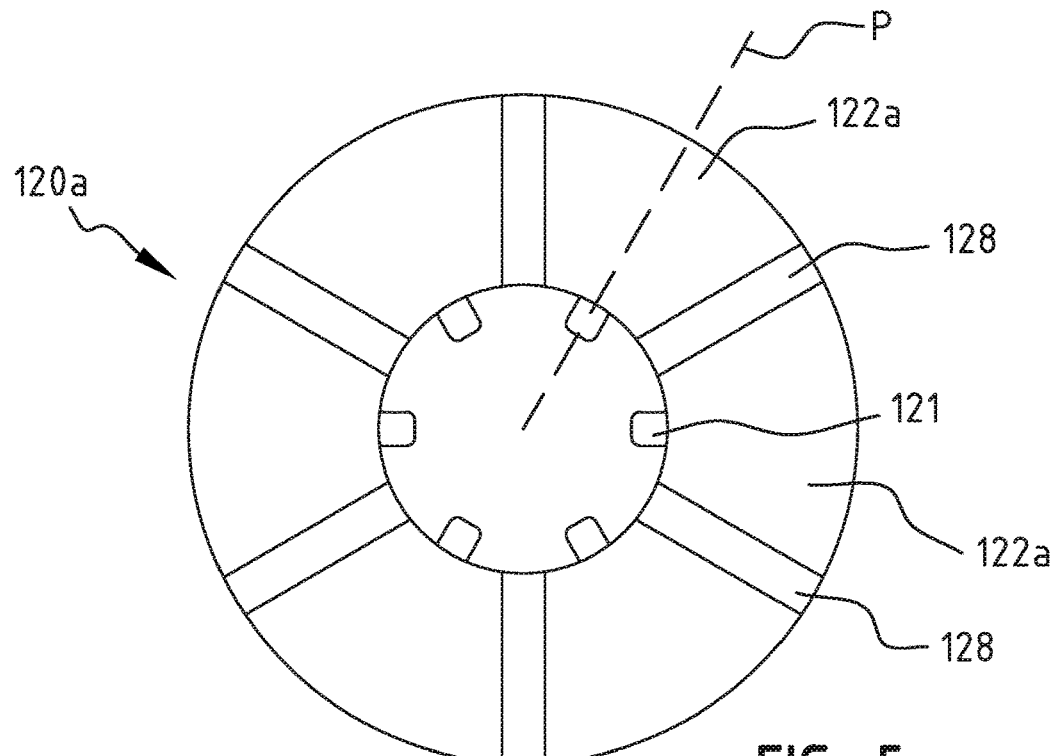
FIG. 5 is a cross-section of an alternative embodiment of a ball member.

The ball member 120 of this example is formed of wedge shape parts 122 which are at least at the more radially outward positions separated from each other to allow the mutual movement. An alternative construction of a ball member 120a is shown in FIG. 5, wherein the wedge shaped parts 122a are interconnected by a softer material 128 for allowing the relative movement of the parts 122a. Also in this embodiment, the engaging members 121 are aligned along the median planes P of the wedge shaped parts 122a for efficient transfer of the compression to the engaging members 121.

Figure 6:
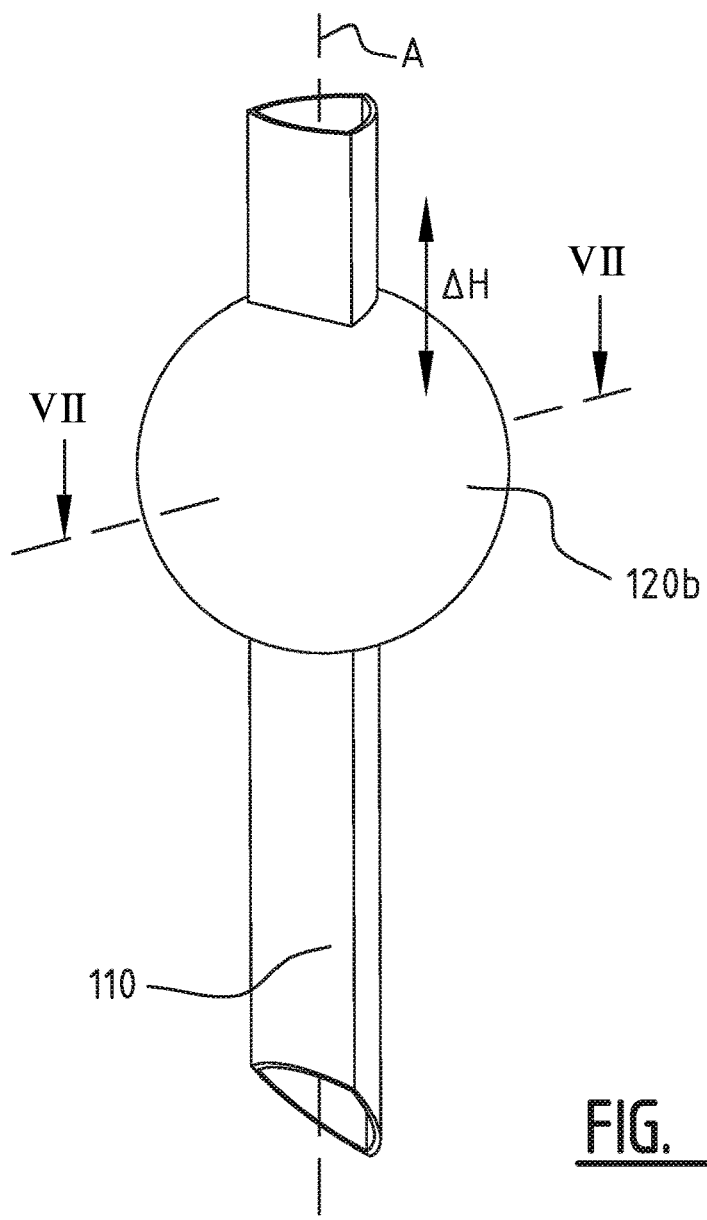
FIG. 6 is a perspective view of an alternative embodiment of the trocar.

In the above described example, the engaging members 121, the ball member 120 and the tube 110 are formed integrally or are at least interconnected, for instance by gluing. In the example of FIGS. 6 and 7 however, the ball member 120b is formed as a separate ball shaped piece provided with a through hole having a shape and size corresponding to the outer surface of the tube 110, in this example substantially triangular as already mentioned earlier. The polygonal shape prevents any rotation of the ball member 120b around the longitudinal axis A of the tube 110. The ball member 120b is this example is made from a relatively soft material, such that a construction of wedge shaped parts as described above is not needed, although this construction is not excluded. Compression of the ball member 120b, indicated with the arrows R in FIG. 7, will thus result in the movement of the engaging members 121 provided on the edges of the triangular cross-section of the tube 110. As the ball member 120b is formed as a separate part, the position of the ball member 120b along the longitudinal axis A of the tube 110 can thus be adjusted, indicated with the arrow ΔH. Movement of the ball member 120b allows adjustment of the insertion depth of the tube 110 in a patient, while still ensuring in a pivot point close to the insertion, i.e. close to the patient.

Figure 8:
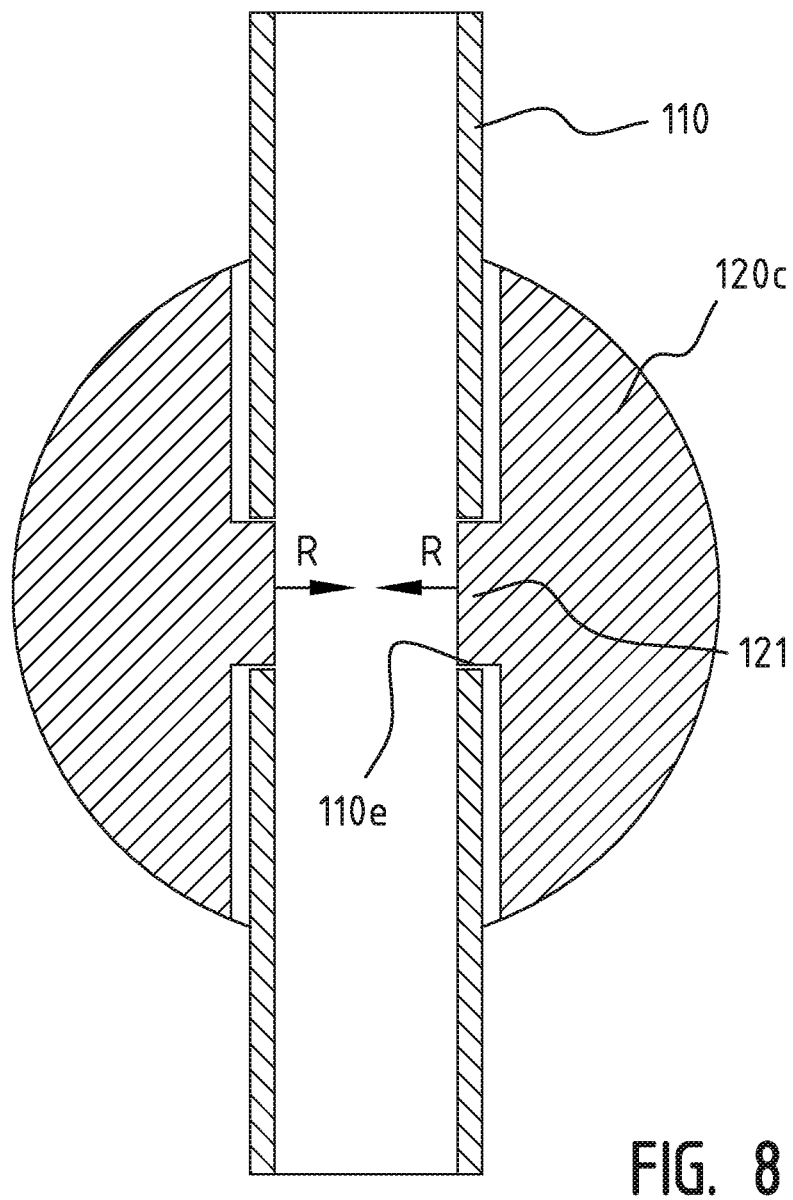
FIG. 8 is a cross-section of another embodiment of the trocar.

Another alternative is shown in cross-section in FIG. 8, wherein a ball member 120c is shown onto which the engaging members 121 are provided. The tube 110 is hereby provided with through holes 110e, through which the engaging members 121 extend for engaging an instrument (not shown) held in the tube 110.

With reference to FIG. 9, the inner diameter of the tube 100 of the trocar 100 preferably closely matches the outer diameter of an instrument to be held. This reduces any play of the instrument and ensures a substantially linear movement, i.e. along the longitudinal axis A of the trocar 100. To however also be able to accommodate instruments having a smaller diameter, it is preferred to provide an adapter 140 which can be inserted into the tube 110 of the trocar 100. The adapter is substantially tube shaped and is preferably provided with an upper flange 141 to rest upon an upper rim 110f of the tube 110. The tubular body 140 has a length h3 which is at least equal to or larger than the distance h3 between the upper rim 110f of the trocar 100 and the engaging members of the trocar 100. Along at least a length of the tubular body 140, incisions 143 are provided to form a plurality of lips 142 which can be moved radially inwardly upon engagement of the engaging members in connected situation. This allows also instruments having a smaller diameter, preferably corresponding to the inner diameter of the tubular body 140, to be firmly engaged and clamped with the trocar 100.

As mentioned above, is the ball member 120 of the trocar 100 specifically arranged for cooperation with a joint device 200 to allow the user to rotate the trocar 100. This joint device 200 is shown in FIGS. 10-13. Other trocars with ball shaped members may however also be used with the joint device. The joint device 200 is provided with a housing 201 (shown in phantom in FIG. 10) wherein a clamping member 202 is held. The clamping member 202 is looped shaped and is made from a resilient and at the same time hard material, in this example stainless steel. Near a first end 202a of the loop shaped clamping member 202, a protrusion 202c is provided which is received in a correspondingly shaped recess 204 of the housing 201. This substantially immobilizes the end 202a. The clamping member extends in a loop 202c, of which the diameter substantially corresponds to the outer diameter of the ball member 120 of the trocar 100. At the opposite end 202b, the clamping member is provided with a receptacle 203.

The receptacle 203 is arranged to receive a widened end portion 302 of a driving rod 301, in this example from a cover device 300 as will be explained in greater detail below. The driving rod 301 is actively moved, as will also be explained in greater detail below, along its longitudinal axis, indicated with the arrow C in FIG. 10. The widened end portion 302 is hereby movable between an extended position, in which the end portion 302 extends at a distance from the end surface, for instance the rim 305 of the cover device 300, and a retracted position, wherein the end portion extends at a smaller distance with respect to this end surface. The receptacle 203 is substantially cup shaped and is provided with hook shaped members 203a for engaging around the widened end portion 302, such that movement of the driving rod 301 will also force the receptacle 203, and thereby the clamping member 202, to move. As shown in phantom in FIG. 10, the housing 201 is provided with an opening 206 aligned with an opening in the cup shaped receptacle 203 such that the driving rod 301 with the end portion 302 can be introduced in the receptacle through this opening 206 with an insertion direction as indicated with the arrow B in FIG. 10. The opening 206 in the housing 201 is more clearly visible in FIG. 1.

As the end 202a of the clamping member 202 is substantially stationary, a movement of the driving rod 301 in a direction of C1 in FIG. 11 will result in the receptacle to move in the same direction, thereby tensioning the clamping member, including the loop shaped part 202c, indicated with the arrows C2 and C3. This will result in a decreased diameter, thereby compressing, indicated with arrows R, the ball shaped member 120 of the trocar 100, and thereby urging the engaging members 121 onto the instrument 500. This locks the ball member 102, and thereby the trocar 100, with respect to the joint member 200 on the one hand and will lock the instrument 500 with respect to the ball member 120, and thus the trocar 100, on the other hand.

In the loosened position, the instrument 500 will be movable with respect to the ball member, dependent on the amount of clamping action by the engaging members 121. Also the ball member 120 and the clamping member may then be movable, such that the ball member 120 and the loop shaped clamping member 202 form a rotation joint. In other words, the trocar 100 may be rotated with respect to the joint member over the spherical surface of the ball member within the boundaries defined by the tube 110, indicated with the arrows C in FIG. 10.

Movement of the driving rod 301 in the direction C1 will also urge the joint device 200 onto a connected device, in this example the cover device 300. The joint device 200 is provided with an annular rim 205 at one end of the housing 201, such that in the opening of the annular rim the driving rod 301 can be received. The rim 204 may be interrupted by to the opening 206 provided in the housing 201. The annular rim 205 has a tapered shape, see in particular the cross-section in FIG. 11, which can be received in a correspondingly shaped recess 305 in the end surface of the housing 304 of the cover device 300. The tapered rim 205 will lock the joint device 200 and the cover device 300 when urged together. If the driving rod 301 is however moved outwardly, the joint device 300 may move in a direction opposite arrow C1 with respect to the cover device 300, thereby loosening the locking action of the tapered rim 205 in the annular recess 305. This will allow the joint device 200 to be rotated along rotation axis A2 (arrow D in FIG. 10), which corresponds to the longitudinal axis of the driving rod 301 and the central axis of the annular rim 205.

FIGS. 12a and 12b show two cross-sections of alternatives of the clamping member 202 in combination with the ball member 120 of the trocar 100. As shown in FIG. 12a, two flanges 202d are provided on the upper, respectively lower edge of the clamping member 202, such that the ball member 120 is contacted with these flanges. This will result in a local point load (seen in the cross-section) and possibly elastic deformation of the ball member 120, in contrast with for instance a planar contact. This improves the interlocking of the clamping member 202 and the ball member 120. In addition thereto, or as an alternative, the clamping member 202 may be provided with a protruding ring shaped member 202e which is fitted in a correspondingly shaped recess for locally deforming the ball shaped member 120 as shown in FIG. 12b.

An alternative clamping mechanism is shown in FIG. 13. In this example, a substantially U-shaped clamping member 202f is provided which partially surrounds the ball member 120. Also a stationary part 209 is provided, which is formed to have a substantially complementary contacting surface. Movement of the clamping member 202f in a direction indicated with C1 will thus result in clamping of the ball member 120, thereby locking preferably both the trocar 100 and the instrument therein. As an alternative, or in addition thereto, also the part 209 may be moved, for instance in the direction indicated with C4 to induce a clamping action.

With reference to FIGS. 14-16, a cover device 300 will be described, which is arranged with a tubular sleeve 390 for covering the parts proximal to the cover device 300. This has the advantage that only the cover device 300, the joint device 200 and the trocar 100 need to be provided sterile, while for instance the driving device 400 and the support frame connected thereto, which are difficult to sterilize, are covered by the sleeve 390. The sleeve 390 is substantially tubular, wherein a first edge 391 thereof is clamped between two housing parts 304a and 304b of the cover device 300, see in particular FIG. 15. Housing parts 304a and 304b are connected using a suitable snap-fit connection.

The housing 304 of the connecting device 300 has the shape of a tube or bushing with a distal end 307, which is provided with the annular groove or recess 305, and a proximal or entry end 306. The proximal end 306 is to be connected to the driving device 400, in particular an end surface 406 thereof. In order to transfer the driving movement of the driving rod 401 of the driving device 400, a transfer member 308 is provided which is movable (indicated with the arrow D in FIG. 16a) with respect to the cover device 300, in particular the housing 304 thereof. The driving rod 301 of the cover device is connected to this transfer member 308. The movement of the transfer member 308 within the cover device 300 is limited by the end surface 307 of the device when in contact with an end surface 308a (see FIG. 16c) of the transfer member 308 and the surface 302a of the widened portion 302 contacting the end surface 307.

Figure 16C:
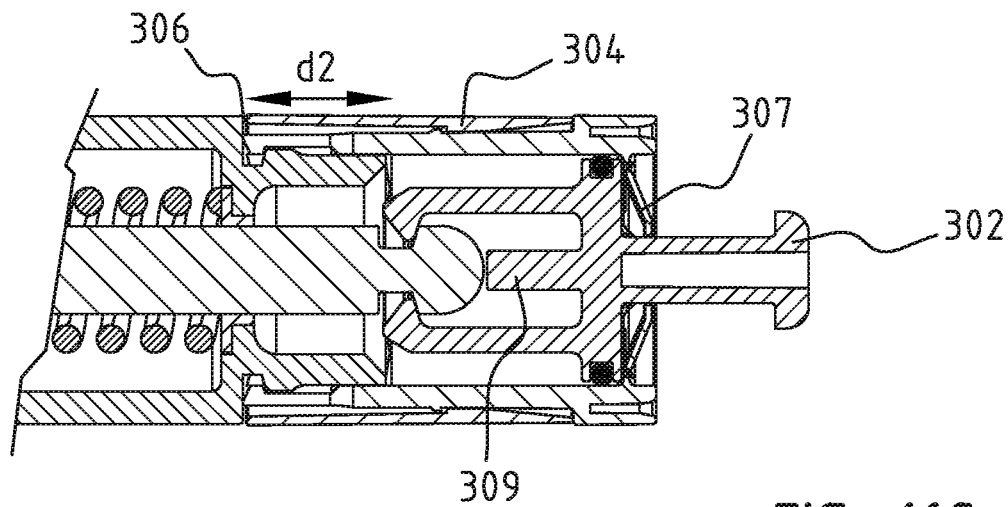

The other end (the end opposite the driving rod 301) is provided with a receptacle for receiving the end 402 of the driving rod 401 of the driving device 400. The end 402 is again provided with a widened end part 402. The driving rod 401 is again moveable with respect to the driving device 400 between a retracted position, shown in FIGS. 16a and 16b for example, and an extended position, see FIG. 16c. Upon interconnection of the driving device 400 and the cover device 300, the transfer member 308 will in this example be pushed to the right with respect to the situation as shown in FIG. 16a by the widened member 402. In this situation, the transfer member 308 is located at the end 307 of the cover device 300, opposite the entry opening 306.

The receptacle of the transfer member 308 is in this example formed by two hook shaped members 310a,b which can bend outwardly (indicated with the arrows e in FIG. 16b), such that upon extension of the driving rod (see FIG. 16c), the hooks 310a,b bend outwardly such that the widened portion 402 can pass. The hooks 310a, b will return to their resting position after passage of the widened portion 402, as shown in the situation of FIG. 16c.

Figure 16D:
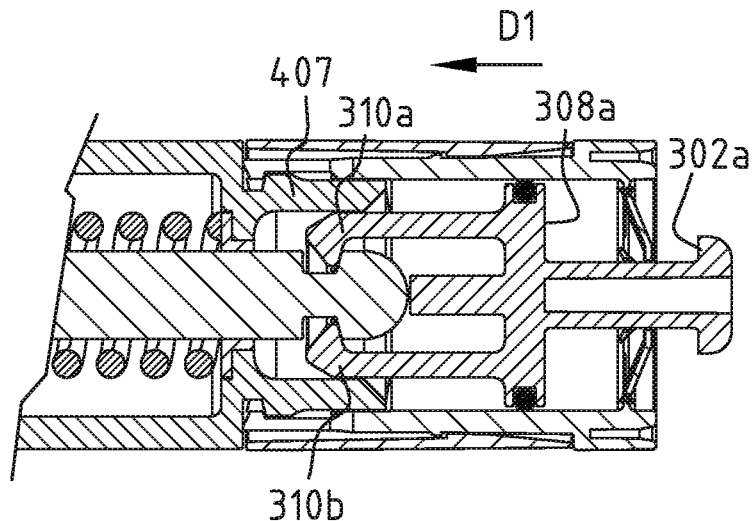

The cover device 300 is thus arranged such that the widened portion 402, at least in extended position of the driving rod 401, is allowed to contact and engage the transfer member 408 even when the transfer member 308 is located at the opposite end 307 of the cover device 300, i.e. the end 307 opposite the entry end 306. The maximum distance d2 (see FIG. 16c) between the entry end 306 and the receptacle therefore corresponds to the entry depth of the widened end portion 402 of the driving rod 401. With reference to FIG. 16d, the driving rod 401 can now be retracted and moved in the direction of the entry opening 306, thereby also moving the transfer member 308 in the same direction D1. Movement of the driving rod 401 will thus result in a corresponding movement of the driving rod 301.

In the depicted embodiment, the end surface 406 of the driving device 400 is provided with an annular rim 407 having an inner diameter d3 (see FIG. 16a) which corresponds to the outer dimensions of the hook shaped members 310a, b in resting position. When the transfer member 308 is retracted towards the entry end 306, the receptacle in the form of the hooks 310a,b is drawn into the annular rim 407, thereby preventing outwardly bending of the hooks. This prevents loosening of the driving rod 401 from the transfer member 408. It is also possible that the annular rim 407 is provided on the cover device 300 near the entry end 306 thereof.

With reference to FIGS. 17-19, the functioning of the driving device 400 will be explained. The driving device 400 is provided with a housing 404 with a substantially tubular shape, having a diameter corresponding to the diameters of the housings of the cover device and the joint device. The distal end 406 is provided with the already mentioned rim 407. The driving rod 401 with widened end 402 extends from the distal end 406 and is moveable along its longitudinal axis A3.

At a more proximal region, the driving rod 401 is provided with a flange 401a onto which a spring 408 engages. Spring 408 is provided between the end surface 406 and the flange 401a and urges the driving rod 401 in a direction indicated with g in FIG. 17. The driving rod 401 is thus biased towards the retracted position, i.e. the widened end portion 402 is urged towards the end surface 406. Further movement inwardly is blocked by abutment of an extension 401b on a driving bushing 409, which will be explained in greater detail below.

The extension 401b is shaped so as to accommodate two pushing members 413 which are associated with a handle 411 and which are in engagement with the flange 401a. Movement of the handle in a direction indicated with h in FIG. 18 will rotate the pushing members 413 (arrows i) and urge the flange 401a and thereby the driving rod 401 in a direction contrary to direction g. The handle 411 is biased towards the extended position by a spring 412. This handle 411 allows manual movement of the driving rod 401, wherein pressing the handle 411, i.e. moving the handle 411 in the direction h, will result in an extension of the widened end 402 from the end surface 406.

The driving device 400 is further provided with a rotation motor 405. As the axle 405a of the motor 405 extends in the driving bushing 409 and a part 405b of the axle 405a is provided with external threading which engages threading on the inner surface of the driving bushing 409, rotation of the axle 405a will result in a translating movement of the driving bushing 409. To prevent rotation of the driving bushing 409, guides 410 are provided which engage in correspondingly shaped grooves in the external surface of the bushing 409 or a flange thereof. It will be clear that rotation of the motor 405 will result in the movement of the driving rod 401 via the driving bush and the extension 401b in abutment therewith. To limit the movement of the driving rod 401, a protrusion 413 is provided on the axle 405a which is moveable between two engaging surfaces, for instance both sides of a protrusions 414 formed on the inner surface 404a of the housing 404, see FIG. 19. Rotation is hereby limited to the movement indicated with the arrow j.

The driving device 400 is further provided with control means 412 which are arranged to control the operation of the motor 405. The control means 412 further comprise storage means, for instance in the form of a memory, to store motor usage history. Actuation of the motor, including direction and duration, may for instance be stored. A unique identifier, for instance a serial number, of the driving device 400, in particular the motor 405, is further stored in the memory. The control means 412 is provided with a connector 414 to connect the control means 412 to a computer or similar device for reading out the data stored in the memory. Another connector 414, or perhaps the same connector 415, may be used to connect an external actuator, for instance in the form of a button for remotely controlling the motor 405.

The present invention is not limited to the embodiment shown, but extends also to other embodiments falling within the scope of the appended claims.

The invention claimed is:

1. A guiding tube for receiving and guiding a medical instrument, wherein the guiding tube comprises engaging members for engaging an instrument inside the tube, a non-circular cross-section at at least the location of said engaging members and a substantially spherically shaped ball member provided on an outer surface of said tube, wherein the engaging members are provided movable with respect to the tube in a direction having a radial component, seen with respect to the longitudinal axis of the tube, upon compression of the ball member.

2. The guiding tube according to claim 1, wherein the ball member comprises a plurality of mutually movable, substantially wedge shaped parts, wherein the wedge shaped parts form the ball member.

3. The guiding tube according to claim 2, wherein the engaging members are located at a radially inward end of at least one of the wedge shaped parts.

4. The guiding tube according to claim 3, wherein the inward end of the at least one of the wedge shape parts has a height, seen in the direction of the longitudinal axis of the tube, that is larger than a height of the engaging member, wherein the at least one of the wedge shaped parts comprises a bridge part for connection with the tube at the inward end, wherein a height of the bridge part corresponds to the height of the engaging member.

5. The guiding tube according to claim 2, wherein each wedge shaped part comprises two side walls under angle with respect to each other, the side walls being shaped as a circular segment having an inner edge and an arc shaped outer edge, wherein the arc shaped outer edges define a substantially spherical surface of the ball member.

6. The guiding tube according to claim 5, wherein two side walls in each wedge shaped part are interconnected by an arc shaped connecting rib at the equatorial plane of the ball, wherein the arc shaped connecting rib is countersunk with respect to the arc shaped outer edges of the side walls.

7. The guiding tube according to claim 2, wherein radially inward ends of the wedge shaped parts are interconnected and wherein the wedge shaped parts extend at mutual distances with respect to each other at a radially outwardly location.

8. The guiding tube according to claim 2, wherein wedge shaped parts of a first relatively stiff material are interconnected by a relatively flexible second material, wherein the first and second materials together form the ball member.

9. The guiding tube according to claim 1, wherein the engaging members are formed integrally on an inner surface of the tube.

10. The guiding tube according to claim 9, wherein the tube has a varying radius seen along the perimeter, defining wall sections having larger radii and wall sections having smaller radii, wherein the engaging members are located on either the wall sections having the larger radii or the wall sections having the smaller radii.

11. The guiding tube according to claim 9, wherein the tube has a substantially polygonal cross-section, preferably triangular, wherein edges of the polygonal cross-section are arc shaped and wherein the engaging members are located at midpoints of said edges.

12. The guiding tube according to claim 1, wherein the ball member is formed integrally with the guiding tube.

13. The guiding tube according to claim 1, wherein the ball member is formed as a separate piece and is provided with a through hole substantially corresponding to the outer shape of the tube.

14. The guiding tube according to claim 13, wherein the engaging members are formed integrally with the ball member and wherein the tube is provided with corresponding through holes for receiving the engaging members.

15. The guiding tube according to claim 1, wherein the engaging members are formed integrally with the guiding tube.

16. The guiding tube according to claim 1, further comprising an adapter tube inserted into the guiding tube, the adapter tube having an outer diameter corresponding with the inner diameter of the guiding tube, wherein at least a part of the wall of the adapter tube at the location of the engaging members is moveable for engaging an instrument.

17. A joint device for holding the guiding tube according to claim 1, wherein the joint device comprises a clamping member arranged for engaging the ball member of the guiding tube, wherein the clamping member is moveable between a locked position wherein the ball member is firmly clamped for locking movement of the ball member with respect to the clamping member and a movable position, wherein the ball member is movable with respect to the clamping member for rotating the guiding tube.

18. A joint device according to claim 17,
wherein the clamping member comprises a receptacle for receiving a connecting member of a driving rod of a connected device, wherein the driving rod is movable between an extended and a retracted position for moving the clamping member between the positions;
wherein the receptacle is arranged to receive the driving rod such that the driving rod extends parallel to a central axis of an annular rim and wherein the central axis extends under an angle with respect to a central axis of the clamping member, wherein the joint device is arranged to allow rotation around the central axis of the annular rim with respect to the connected device in the extended position of the driving rod; and
wherein a of the joint device or the connected device has a tapered end, and wherein a rim of the other of the joint device or the connected device has a correspondingly shaped end.

19. The joint device according to claim 18, wherein the rims of the joint device and the connected device are provided with cooperating toothing.

20. The joint device according to claim 17, wherein the clamping member comprises a contacting surface arranged for contacting the ball member, wherein the contacting surface is provided with at least one protrusion or a plurality of protrusions for engaging the ball member along at least a part of the circumference of the ball member.

21. A cover device arranged to be connected between a joint device according to claim 17 and a driving device and which is arranged to transfer the movement of a driving rod from the driving device to the joint device, wherein the cover device comprising a tubular covering sleeve for covering a connected device, such as the driving device, wherein one end of the sleeve is closed and sealed to the cover device and wherein another end is open so as to cover the connected device and possibly other equipment such as a holding frame.

22. The cover device according to claim 21,
wherein the cover device comprises a transfer member which is movable with respect to the cover device for transferring the movement of the driving rod of the driving device in a connected state, wherein a first end of the transfer member is arranged for receiving a connecting member, for instance a widened end portion, of the driving rod and wherein the opposite second end comprises a connecting member for connecting to the joint device, wherein said connecting member is movable between a retracted and extended position with respect to the cover device; and
wherein the first end of the transfer member comprises mutually movable hook shaped members for engaging the connecting member, wherein the hook shaped members are movable between an insertion position wherein the hook shaped members are at a distance allowing the connecting member to pass, and an engaged position wherein the hook shaped members engage the driving rod behind the connecting member.

23. The cover device according to claim 22, further comprising locking means for locking the hook shaped members in the engaged position, wherein the locking means are positioned for locking the hook shaped members in the retracted position of the driving rod.

24. The cover device according to claim 23, wherein the locking means comprise an annular rim for receiving the hook shaped members in the retracted position for limiting outwardly movement of said hook shaped members.

25. The cover device according to claim 24, wherein the annular rim is provided in the cover device at and end towards the first end of the transfer member.

26. A combination of a driving device comprising a driving rod which is moveable between a retracted and an extended position and a cover device according to claim 21, wherein the cover device is arranged such that the driving rod of the driving device is connectable to a first end of a transfer member in an extended position of a connecting member of the transfer member.

27. A driving device for use with the joint device according to claim 17, wherein the driving device comprising a housing and a driving rod provided with a connecting member at its end, wherein the driving device is further provided with moving means for moving the driving rod between an extended position and a retracted position, both with respect to the housing.

* * * * *